(12) United States Patent
Weeber et al.

(10) Patent No.: US 8,747,466 B2
(45) Date of Patent: Jun. 10, 2014

(54) INTRAOCULAR LENS HAVING EXTENDED DEPTH OF FOCUS

(75) Inventors: Hendrik A. Weeber, Groningen (NL); Patricia Ann Piers, Groningen (NL)

(73) Assignee: AMO Groningen, B.V., Groningen (NL)

( * ) Notice: Subject to any disclaimer, the term of this patent is extended or adjusted under 35 U.S.C. 154(b) by 0 days.

(21) Appl. No.: 12/197,249

(22) Filed: Aug. 23, 2008

(65) Prior Publication Data
US 2009/0187242 A1 Jul. 23, 2009

Related U.S. Application Data

(60) Provisional application No. 60/968,250, filed on Aug. 27, 2007.

(51) Int. Cl.
*A61F 2/16* (2006.01)
(52) U.S. Cl.
USPC .......................... 623/6.28; 623/6.24; 623/6.3
(58) Field of Classification Search
USPC ........................................ 623/6.24, 6.27, 6.3
See application file for complete search history.

(56) References Cited

U.S. PATENT DOCUMENTS

| | | | |
|---|---|---|---|
| 3,367,734 A | 2/1968 | Bystricky et al. | |
| 4,637,697 A | 1/1987 | Freeman | |
| 4,642,112 A * | 2/1987 | Freeman | 623/6.3 |
| 4,655,565 A | 4/1987 | Freeman | |
| 4,778,462 A | 10/1988 | Grendahl | |
| 4,795,462 A | 1/1989 | Grendahl | |
| 4,798,608 A | 1/1989 | Grendahl | |
| 4,798,609 A | 1/1989 | Grendahl | |
| 4,932,970 A | 6/1990 | Portney | |

(Continued)

FOREIGN PATENT DOCUMENTS

| | | |
|---|---|---|
| EP | 343067 A1 | 11/1989 |
| EP | 457553 A2 | 11/1991 |

(Continued)

OTHER PUBLICATIONS

Cohen, Allen L., "Pratical design of a bifocal hologram contact lens or intraocular lens", Book, Jul. 1, 1992, pp. 3750-3754, vol. 31, No. 19, Optical Society of America, Richmond, Virginia.

(Continued)

*Primary Examiner* — David H Willse
*Assistant Examiner* — Tiffany Shipmon
(74) *Attorney, Agent, or Firm* — AMO Groningen, B.V.

(57) ABSTRACT

An intraocular lens is disclosed, which includes a diffractive element with a relatively low add power. The add power may be less than about 2 Diopters, may be less than about 1 Diopter, or may be in the ranges of 0.5 to 2.5 Diopters, or 1.0 to 2.0 Diopters, or 1.5 to 2.0 Diopters, or 1.0 to 1.5 Diopters. The low-add-power diffractive element increases the depth of the focus of the intraocular lens, for example, compared to a similarly shaped intraocular lens without the diffractive element. In one embodiment, the depth of focus is defined in terms of a threshold MTF value at a particular spatial frequency. The threshold may be an absolute threshold, such as 0.10, 0.15, 0.17, 0.20, 0.25 or 0.30, or may be a relative threshold, such as a particular percentage of the peak value. The spatial frequency may be 25 line pairs per mm, 50 line pairs per mm, 100 line pairs per mm, or any suitable value.

22 Claims, 23 Drawing Sheets

(56) References Cited

U.S. PATENT DOCUMENTS

| | | |
|---|---|---|
| 4,995,714 A | 2/1991 | Cohen |
| 4,995,715 A | 2/1991 | Cohen |
| 5,016,977 A | 5/1991 | Baude et al. |
| 5,056,908 A | 10/1991 | Cohen |
| 5,066,301 A | 11/1991 | Wiley |
| 5,089,023 A | 2/1992 | Swanson |
| 5,096,285 A * | 3/1992 | Silberman .................... 351/161 |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,144,483 A | 9/1992 | Cohen |
| 5,225,858 A | 7/1993 | Portney |
| 5,229,797 A | 7/1993 | Futhey et al. |
| 5,652,638 A | 7/1997 | Roffman et al. |
| 5,699,142 A | 12/1997 | Lee et al. |
| 5,748,282 A | 5/1998 | Freeman |
| 5,760,871 A | 6/1998 | Kosoburd et al. |
| 5,796,462 A | 8/1998 | Roffman et al. |
| 5,968,094 A | 10/1999 | Werblin et al. |
| 6,126,283 A | 10/2000 | Wen et al. |
| 6,126,286 A | 10/2000 | Portney |
| 6,142,625 A | 11/2000 | Sawano et al. |
| 6,210,005 B1 | 4/2001 | Portney |
| 6,338,559 B1 | 1/2002 | Williams et al. |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,609,793 B2 | 8/2003 | Norrby et al. |
| 6,705,729 B2 | 3/2004 | Piers et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,923,539 B2 * | 8/2005 | Simpson et al. .......... 351/160 R |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,441,894 B2 | 10/2008 | Zhang et al. |
| 7,475,986 B2 | 1/2009 | Dai et al. |
| 7,615,073 B2 | 11/2009 | Deacon et al. |
| 7,871,162 B2 | 1/2011 | Weeber |
| 2002/0118337 A1 | 8/2002 | Perrott et al. |
| 2003/0076478 A1 | 4/2003 | Cox |
| 2003/0171808 A1 | 9/2003 | Phillips |
| 2004/0021824 A1 | 2/2004 | Ye et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 * | 8/2004 | Piers et al. .................... 351/168 |
| 2004/0230299 A1 | 11/2004 | Simpson et al. |
| 2005/0096226 A1 | 5/2005 | Stock et al. |
| 2005/0128432 A1 | 6/2005 | Altmann |
| 2005/0203619 A1 | 9/2005 | Altmann |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 * | 3/2006 | Blum et al. ................... 351/159 |
| 2006/0098162 A1 | 5/2006 | Bandhauer et al. |
| 2006/0098163 A1 * | 5/2006 | Bandhauer et al. ........... 351/161 |
| 2006/0109421 A1 | 5/2006 | Ye et al. |
| 2006/0116763 A1 | 6/2006 | Simpson |
| 2006/0116764 A1 * | 6/2006 | Simpson ..................... 623/6.23 |
| 2006/0176572 A1 | 8/2006 | Fiala |
| 2006/0238702 A1 | 10/2006 | Glick et al. |
| 2006/0244904 A1 | 11/2006 | Hong et al. |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 * | 8/2007 | Hong et al. ................... 351/171 |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0273169 A1 * | 11/2008 | Blum et al. ................... 351/169 |
| 2009/0062911 A1 | 3/2009 | Bogaert |
| 2009/0164008 A1 | 6/2009 | Hong et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0268158 A1 | 10/2009 | Weeber |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0161048 A1 | 6/2010 | Schaper, Jr. |

FOREIGN PATENT DOCUMENTS

| | | |
|---|---|---|
| EP | 681198 A1 | 11/1995 |
| EP | 0926531 A1 | 6/1999 |
| EP | 949529 A2 | 10/1999 |
| EP | 1424049 A1 | 6/2004 |
| EP | 1310267 B1 | 1/2008 |
| EP | 1424049 B1 | 6/2009 |
| WO | WO9222264 A1 | 12/1992 |
| WO | WO9303409 A1 | 2/1993 |
| WO | WO0019906 A1 | 4/2000 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | WO03009053 A1 | 1/2003 |
| WO | WO2004034129 A1 | 4/2004 |
| WO | WO2004090611 A2 | 10/2004 |
| WO | WO2004096014 A2 | 11/2004 |
| WO | WO2005019906 A1 | 3/2005 |
| WO | WO2006025726 A1 | 3/2006 |
| WO | WO2006047698 A1 | 5/2006 |
| WO | WO2006060477 A2 | 6/2006 |
| WO | WO2006060480 A2 | 6/2006 |
| WO | WO2007092948 A1 | 8/2007 |
| WO | WO2007133384 A2 | 11/2007 |
| WO | WO2008045847 A2 | 4/2008 |
| WO | WO2009076670 A1 | 6/2009 |

OTHER PUBLICATIONS

Doskolovich, Leonid L., Golub Mikhail A., Kazanskiy Nikolay L., Soiler Victor A., Uspleniev Gleb V., "Special diffractive lenses", Book, 1992, pp. 393-402, SPIE vol. 1780 Lens and Optical Systems Design, Institute of Unique Instrumentation, Samara, Russia.

International Search Report and Written Opinion for Application No. PCT/IB2011/001067, mailed on Sep. 13, 2011, 13 pages.

Piers P.A., et al., "Eye Models for the Prediction of Contrast Vision in Patients with New Intraocular Lens Designs," Optics Letters, 2004, vol. 29 (7), pp. 733-735.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

(56) References Cited

OTHER PUBLICATIONS

Co-pending U.S. Appl. No. 12/771,550, filed Apr. 30, 2010.
International Search Report for Application No. PCT/IB2009/005590, mailed on Sep. 30, 2009, 3 pages.
International Search Report for Application No. PCT/US08/073999, mailed on Dec. 3, 2008, 3 pages.
International Search Report for Application No. PCT/US2010/061081, mailed on Apr. 6, 2011, 2 pages.
U.S. Appl. No. 12/129,155, filed Apr. 23, 2009.
U.S. Appl. No. 11/618,325, filed Dec. 29, 2006, (Brady et al).
U.S. Appl. No. 11/618,411, filed Dec. 29, 2006, (Bradyetai).
U.S. Appl. No. 12/109,251, filed Apr. 24, 2008.
Alfonso J.F., et al., "Prospective Study of the Acri.LISA bifocal Intraocular Lens," Journal of Cataract Refractive Surgery, 2007, vol. 33 (11), pp. 1930-1935.
Canovas C., et al., "Hybrid Adaptive-Optics Visual Simulator," Optical Letters, 2010, vol. 35 (2), pp. 196-198.
Diffractive Lenses for Extended Depth of Focus and Presbyopic Correction. Presentation from Wavefront Congress held on Feb. 15, 2008, Rochester, New York.
International Search Report for Application No. PCT/EP2008/061235, mailed on Mar. 5, 2009, 4 pages.
International Search Report for Application No. PCT/EP2009/051783, mailed on Apr. 28, 2009, 3 pages.
International Search Report for Application No. PCT/US09/042449, mailed on Nov. 5, 2009, 5 pages.
International Search Report for Application No. PCT/US2010/038167, mailed on Sep. 27, 2010, 2 pages.
Liou H.L., et al., "Anatomically Accurate, Finite Model Eye for Optical Modeling," Journal of Optical Society of America, 1997, vol. 14 (8), pp. 1684-1695.
Marsack J.D., et al., "Metrics of Optical Quality Derived From Wave Aberrations Predict Visual Performance," Journal of Vision, 2004, vol. 4 (4), pp. 322-328.
Monsoriu J.A., et al., "Devil's Lenses," Optics Express, 2007, vol. 15 (21), pp. 13858-13864.
Norrby S., et al., "Model Eyes for Evaluation of Intraocular Lenses," Applied Optics, 2007, vol. 46 (26), pp. 6595-6605.
Piers P.A., et al., "Theoretical Comparison of Aberration-Correcting Customized and Aspheric Intraocular Lenses," Journal of Refractive Surgery, 2007, vol. 23 (4), pp. 374-384.
Siedlecki D., et al., "Radial Gradient index Intraocular Lens: a Theoretical Model," Journal of Modern Optics, 2008, vol. 55 (4-5), pp. 639-647.
Van Meeteren A., "Calculations on the Optical Modulation Transfer Function of the Human Eye for White Light," Optica Acta, 1974, vol. 21 (5), pp. 395-412.
Vanden Berg T.J., "Analysis of Intraocular Straylight, Especially in Relation to Age," Optometry and Vision Science, 1995, vol. 72 (2), pp. 52-59.
Villegas E.A., et al., "Correlation between Optical and Psychophy, Sical Parameters as a Function of Defocus," Optometry and Vision Science, 2002, vol. 79 (1), pp. 60-67.
Co-pending U.S. Appl. No. 12/503,267, filed Jul. 15, 2009.

* cited by examiner

| | | Object | Spectacle | Cornea | Aperture Stop | Lens | Retina | Image |
|---|---|---|---|---|---|---|---|---|
| Axial Length [mm] | 23.45 | | | | | | | |
| Effective Lens Position [mm] | 5.25 | | | | | | | |
| Thickness before surface, t [mm] | | | 1E+98 | 14 | 3.74 | 1.51 | 18.2 | 0.0057602 |
| Thickness after surface, t' [mm] | | 1.00E+98 | 14 | 3.74 | 1.51 | 18.2 | 5.76E-03 | |
| Refractive index before surface, n | | | 1 | 1 | 1.336 | 1.336 | 1.336 | 1.336 |
| Refractive index after surface, n' | | 1 | 1 | 1.336 | 1.336 | 1.336 | 1.336 | |
| Power, phi [mm-1] | | | -0.0005 | 0.0438 | 0 | 0.0212 | 0 | |
| Power, phi [Diopters] | | | -0.5 | 43.8 | 0 | 21.2 | 0 | |
| Marginal ray | | | | | | | | |
| Ray height, y [mm] | | 0 | 1.7950276 | 1.8075928 | 1.5884695 | 1.5 | 0.0004746 | 0 |
| Ray angle before surface, u [radians] | | | 1.80E-98 | 0.0008975 | -0.058589 | -0.058589 | -0.082392 | -0.082392 |
| Ray angle after surface, u' [radians] | | 1.80E-98 | 0.0008975 | -0.058589 | -0.058589 | -0.082392 | -0.082392 | |
| Chief ray | | | | | | | | |
| Ray height, ybar [mm] | | -8.75E+96 | -1.491147 | -0.27676 | 0 | 0.11174 | 1.4262692 | 1.4266853 |
| Ray angle before surface, ubar [radians] | | | 0.0874875 | 0.0867419 | 0.074 | 0.074 | 0.0722269 | 0.0722269 |
| Ray angle after surface, ubar' [radians] | | 0.0874875 | 0.0867419 | 0.074 | 0.074 | 0.0722269 | 0.0722269 | |
| Paraxial constants of eye system | | | | | | | | |
| Numerical aperture | 1.795E-98 | | | | | | | 0.1099506 |
| Field of view [degrees] | 4.999933 | | | | | | | |
| Lagrange invariant [mm] | | | 0.1570425 | 0.1570425 | 0.1570425 | 0.1570425 | 0.1570425 | |

Fig. 3

INTRAOCULAR LENS HAVING EXTENDED DEPTH OF FOCUS

RELATED APPLICATION

The present application claims priority under 35 U.S.C §119(e) to provisional application No. 60/968,250, filed on Aug. 27, 2007 under the same title. Full Paris Convention priority is hereby expressly reserved.

BACKGROUND OF THE INVENTION

1. Field of the Invention

This invention relates generally to intraocular lenses and associated systems and methods, and more specifically to intraocular lenses having an extended depth of focus.

2. Description of the Related Art

There are many medical conditions that degrade the vision of a patient's eye. For instance, cataracts can cause the natural lens of an eye to become opaque. Fortunately, in many of these cases, the natural lens of the eye may be removed surgically and replaced with an intraocular lens, thereby restoring the vision of the eye.

An intraocular lens may be corrected for one or more particular object distances, so that objects at the particular object distance appear in focus, while objects farther away from the particular object distance appear increasingly blurred. The range of distances over which the blurring is acceptable small is known as the depth of focus. There is ongoing effort to improve the depth of focus of intraocular lenses, which can help reduce the dependence on spectacles, contact lenses, or other additional corrective optics.

SUMMARY OF THE INVENTION

The present invention is generally directed ophthalmic devices, systems, and methods for extending the depth of focus of subject's vision. The ophthalmic device may be an intraocular lens, a contact lens, a corneal inlay or onlay, a pair of spectacles, or the like. Alternatively, the ophthalmic device may be a part of the natural eye, for example, the resulting structure of a corneal surface after a refractive procedure such as a LASIK or PRK procedure. One aspect of the present invention involves an ophthalmic devices comprising a first surface having a first shape and an opposing second surface having a second shape. The first and second shapes provide a refractive power. A diffractive pattern is imposed on at least one of the first shape and the second shape. The first and second surfaces together provide a base power, for example, to provide a subject with distant vision for objects at an optical infinity. The first and second surfaces together also provide an add power that is less than a predetermined amount, for example, less than about two Diopters. The add power is generally selected to provide relatively high visual acuity for objects at a distance that is closer than optical infinity. For example, the surfaces may be configured such that the visual acuity of objects at a predetermined distance from the eye of a subject is about the same as objects at optical infinity. In one embodiment, the ophthalmic device has an add power of about 1 Diopter and objects at about 1 meter from the subject have a relatively high visual acuity, for example, about the same visual acuity as objects at optical infinity.

In another aspect of the present invention, an ophthalmic device comprises a first surface having a first shape and an opposing second surface having a second shape. The first and second shapes provide a refractive power. A diffractive pattern is imposed on at least one of the first shape and the second shape so that the intraocular lens has a base power and an add power. The intraocular lens is optically described by a model lens, such that when the model lens is included in an intraocular lens plane of an eye model including a model cornea, the modulation transfer function of the eye model exceeds about 0.17, at a spatial frequency of about 50 line pairs per millimeter, over a range of at least about 1.7 Diopters.

In yet another aspect of the present invention, an ophthalmic device comprises an optic comprising a first surface having a first shape and an opposing second surface having a second shape. The first and second shapes provide a refractive power. A diffractive pattern is imposed on at least one of the shapes so that the optic has a base power and an add power. When the optic is placed in an intraocular lens plane of a physical eye model including a model cornea, the modulation transfer function of the eye model exceeds about 0.17, at a spatial frequency of about 50 line pairs per millimeter, over a range of at least about 1.7 Diopters.

In still another aspect of the present invention, an ophthalmic device comprises a first surface having a first shape and an opposing second surface having a second shape. The first and second shapes provide a refractive power. A diffractive pattern is imposed on at least one of the shapes so that the intraocular lens has a base power and an add power. In some embodiments, the diffractive pattern increases the depth of focus of the intraocular lens when illuminated at a predetermined wavelength by at least about 50% relative to a reference intraocular lens without the diffractive pattern and having substantially the same refractive power and first and second shapes. Alternatively or additionally, the diffractive pattern increases the depth of focus of the intraocular lens when illuminated by a polychromatic light source by at least about 30% relative to a reference intraocular lens without the diffractive pattern and having substantially the same refractive power and first and second shapes.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following figures, with like numerals indicating like parts:

FIG. 3 is a paraxial raytrace of a "typical" eye.

DETAILED DESCRIPTION

Figure 1:
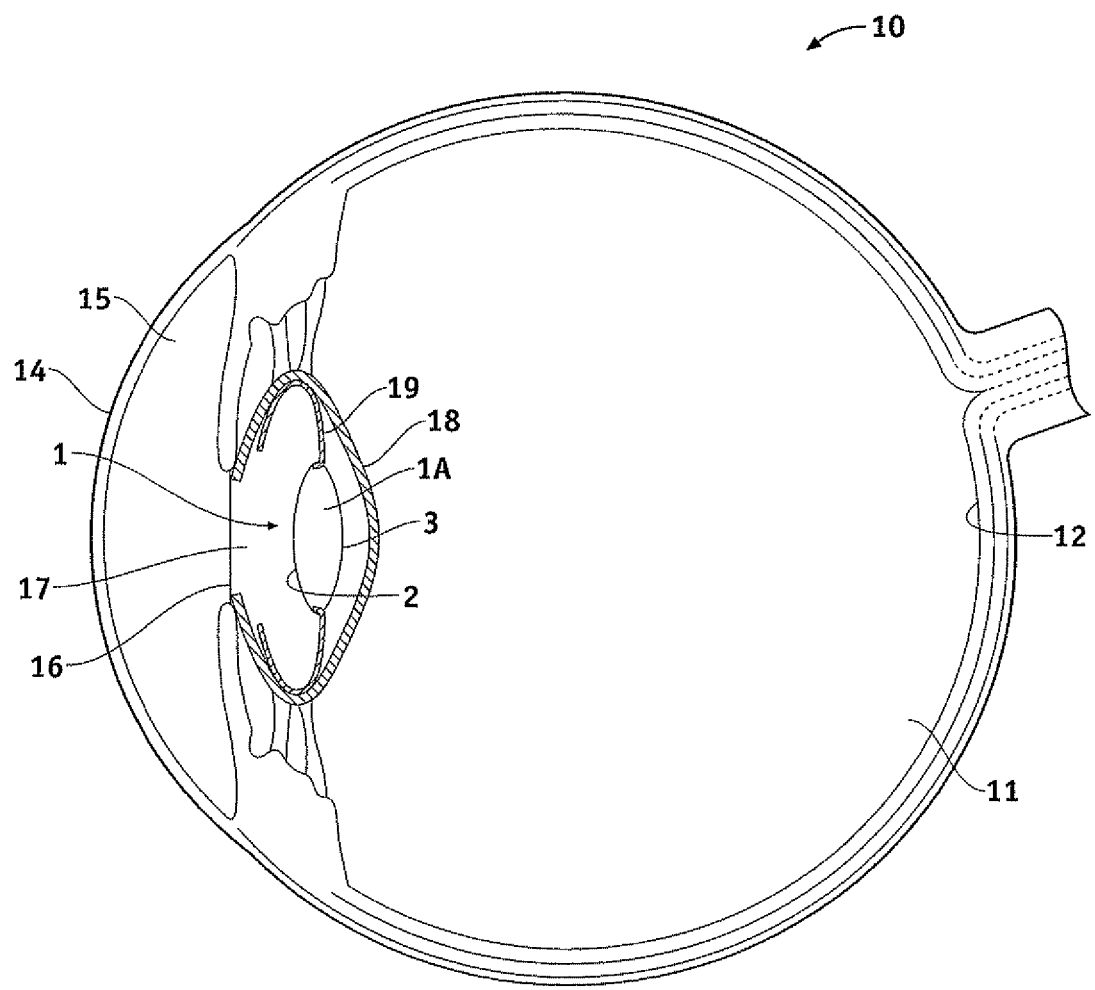
FIG. 1 is a schematic drawing of a human eye after implantation with an intraocular lens.

FIG. 1 shows a human eye 10, after an intraocular lens 1 has been implanted. Light enters from the left of FIG. 1, and passes through the cornea 12, the anterior chamber 15, the iris 16, and enters the capsular bag 17. Prior to surgery, the natural lens occupies essentially the entire interior of the capsular bag 17. After surgery, the capsular bag 17 may house the intraocular lens 1, in addition to a fluid that occupies the remaining volume and equalizes the pressure in the eye 10. The intraocular lens 1 is described in more detail below. After passing through the intraocular lens 1, light exits the posterior wall 18 of the capsular bag 17, passes through the posterior chamber 11, and strikes the retina 12, which detects the light and converts it to a signal transmitted through the optic nerve to the brain.

The intraocular lens 1 has an optic 1a that has a refractive index greater than the fluid that surrounds it. The optic 1a has an anterior surface 2 facing away from the retina 12 and a posterior surface 3 facing toward the retina 12. The optic 1a is held in place by a haptic 19, which couples the optic 1a to the capsular bag 19. In the illustrated embodiment, the optic 1a is suspended within the capsular bag 17, for example, to allow accommodative movement of the optic 1a of the intraocular lens 1 along the optical axis (a so called "accommodative intraocular lens"). Alternatively, the intraocular lens 1 may be disposed adjacent to, and even pressed against, the posterior wall 18, for example, to reduce cellular growth on the optic 1a. The optic 1a may be either a monofocal intraocular lens or a multifocal intraocular lens.

A well-corrected eye forms an image at the retina 12. If the lens has too much or too little power, the image shifts axially along the optical axis away from the retina 12, toward or away from the lens. Note that the power required to focus on a close or near object is more than the power required to focus on a distant or far object. The difference in optical power between the farthest and nearest object than may be brought into focus by a particular lens or lens system is known typically as the "add power" (eg., in the case of a multifocal intraocular lens) or the "range of accommodation" or "accommodative range" (e.g., in the case of an accommodating intraocular lens that responds to ciliary muscle contraction to move axially and/or deform so as to change the optical power of the optic). A normal range of add power or accommodation is about 4 Diopters at the plane of the optic 1a of an intraocular lens, although this number may be as low as 3 or fewer Diopters or as high as 6 or more Diopters, depending on the geometry of the patient's eye.

Figure 2:
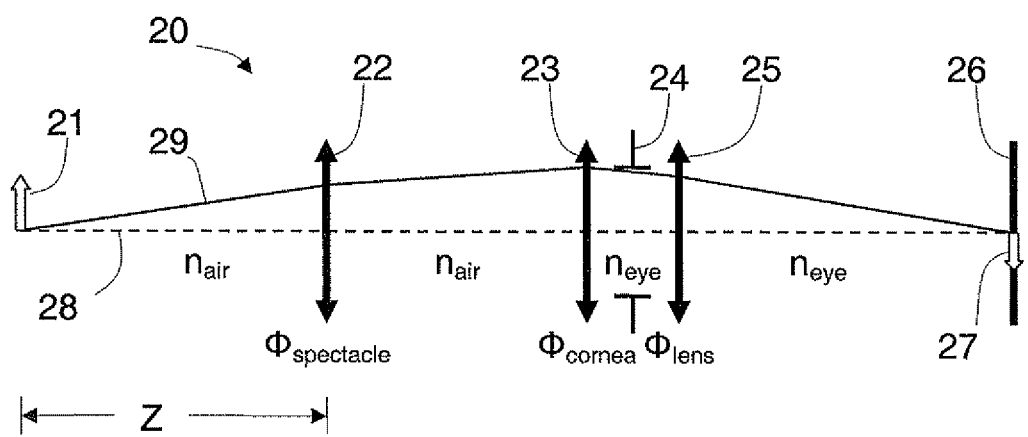
FIG. 2 is a schematic drawing of a thin lens model that approximates the human eye of FIG. 1.

In many cases, the optical system of the eye may be well approximated by a thin lens model, shown schematically in FIG. 2. Such a thin lens system 20 may be used to predict the location of an image for a given object distance Z. In addition, the thin lens system 20 may also be used to predict the power required of a lens to bring objects at an object distance Z into focus on the retina.

A marginal light ray 29 originates at the base of an object 21, where it crosses the optical axis 28. The ray 29 passes through an optional spectacle 22 having a power $\phi_{spectacle}$, and enters the eye. The eye itself is represented by a cornea 23 with a power $\phi_{cornea}$, an aperture stop (or pupil) 24, an intraocular lens 25 with a power $\phi_{lens}$, and a retina 26. An image 27 is formed of the object 21 at the location where the marginal ray 29 intersects the optical axis 28. If the object 21 is "in focus", then the image 27 is formed at the retina 26. If the object is "out of focus", then the image is translated axially away from the retina 26, either too close to the lens or too far from the lens. The space between the object 21 and the cornea 23 is assumed to be filled with air, having a refractive index of $n_{air}$ (typically 1). The space between the cornea 23 and the retina 26 is assumed to be filled with a fluid having a refractive index of $n_{eye}$.

Some specific numbers are included in a paraxial raytrace of a "typical" eye, shown in FIG. 3. In addition to predicting where an image will fall for a given object distance, such a raytrace may be used to generate one of a number of known formulas that predict the required intraocular lens power for a particular patient's eye. Because the utility of such a raytrace may be great, it is beneficial to examine the raytrace methodology and some of its assumptions. The raytrace is described in detail in the following several paragraphs.

The calculations are performed using a paraxial raytrace, with five surfaces: (1) spectacles, (2) the cornea, (3) the intraocular lens, (4) the iris (or aperture stop, or pupil), and (5) the retina. For the purposes of this calculation, each of these five surfaces is assumed to be an infinitely thin surface or thin lens having a particular power, which may be a value including zero. The numerical values used in the calculations may vary depending on the preference of the practitioner, but the thin lens methodology remains essentially unchanged. Each of these surfaces is described in more detail below.

Given the power Φ of each surface, the refractive index n between the surfaces, and thickness t between the surfaces, one may use the well-known paraxial refraction and transfer equations to trace a ray through the optical system of the eye.

The paraxial refraction equation predicts the exiting ray angle (relative to the optical axis) u', after refraction at a surface with power Φ:

$$n'u' = nu - y\phi,$$

where u is the incident ray angle, y is the incident and exiting ray height at the surface, and n and n' are the incident and exiting refractive indices, respectively. The refractive indices are dimensionless, the ray angles are in radians, the ray heights are in mm [or, alternately, m], and the surface powers are in mm$^{-1}$ [or, alternately, Diopters].

The paraxial transfer equation predicts the ray height y' at a surface, after propagation by a distance t between a previous surface and the current surface:

$$y' = y + tu,$$

where y is the ray height at the previous surface and u is the ray angle (relative to the optical axis) between the previous surface and the current surface. The ray angle is in radians and the ray heights and distances are both in mm [or, alternately, both in m].

The above paraxial refraction and transfer equations are alternately used to trace rays through a multi-surface optical system. The equations above trace rays from left-to-right, but may easily be inverted to trace rays from right-to-left.

There are two commonly used rays shown in the raytrace: (1) a marginal ray, which originates from the base of the object, passes through the edge of the aperture stop, and strikes the base of the image, and (2) a chief ray, which passes through the center of the aperture stop and extends to the edge of the field of view. Quantities that may be entered by the user are shown in thick-bordered cells; the remaining quantities are calculated. Note that several distances are calculated with respect to measurable or predictable quantities in the eye, such as Axial Length (AL) and Effective Lens Position (ELP). A Vertex Distance (VD) is the distance between the spectacle and the cornea, and is taken to be 14 mm in this example. The object distance ("Z" in FIG. 2) may be infinite.

Once the rays are traced, one may use the raytrace results to derive a known formula for the required lens power $\Phi_{lens}$ for a given set of distances AL, ELP and VD, an infinite object distance, a given cornea power $\Phi_{cornea}$, and a given (optional) spectacle power $\Phi_{spectacle}$ power:

$$\phi_{lens} = \frac{n_{eye}}{AL - ELP} - \frac{n_{eye}}{\frac{n_{eye}}{\frac{n_{air}}{\frac{n_{air}}{\phi_{spectacle}} - VD} + \phi_{cornea}} - ELP}$$

For the model, the cornea is then assumed to be a single, infinitely-thin surface, with an optical power of $(n_{cornea} - n_{air})/R_{cornea}$. A typical measured value for the radius of curvature of the cornea is about 7.704 mm, which yields a typical power of (1.3375−1)/(7.704 mm)=0.0438 mm$^{-1}$, or 43.8 Diopters. For the model, the incident medium for the cornea is air, with a refractive index of 1. The exiting medium of the cornea is typically chosen to be the refractive index of the eye $n_{eye}$, with a value of roughly 1.336. Note that the value of $n_{cornea}$ is used only to calculate the power of the cornea, and is not used at its exiting medium. In tracing rays between the cornea and the lens, the refractive index is taken to be $n_{eye}$, or about 1.336.

Common, off-the-shelf, intraocular lenses are available from powers of 5 Diopters to 30 Diopters, in increments of 0.5 Diopters. Some manufacturers may even provide increments as small as 0.25 Diopters, or smaller. The above formula is commonly used to estimate the required lens power, and the closest available off-the-shelf lens power is typically chosen for implantation.

The numerical values themselves are for a so-called "typical" eye, although any suitable values may be used. For typical values of axial length and effective lens position, 23.45 mm and 5.25 mm, respectively, a typical separation between the intraocular lens and the retina is about 18.2 mm. The incident refractive index on the retina is $n_{eye}$, or about 1.336.

As a numerical example, consider the following typical values: $n_{air}$=1, $n_{cornea}$=1.3375, $N_{eye}$=1.336, $R_{cornea}$=7.704 mm, $\Phi_{cornea}$=0.0438 mm$^{-1}$ (or 43.8 D), $\Phi_{spectacles}$=−0.0005 mm$^{-1}$ (or −0.5 D), VD=14 mm, ELP=5.25 mm, and AL=23.45 mm. Inserting these numerical values into the equation for the required power $\Phi_{lens}$ of the intraocular lens gives a typical value of 0.0212 mm$^{-1}$ (or 21.2 D).

Figure 4:
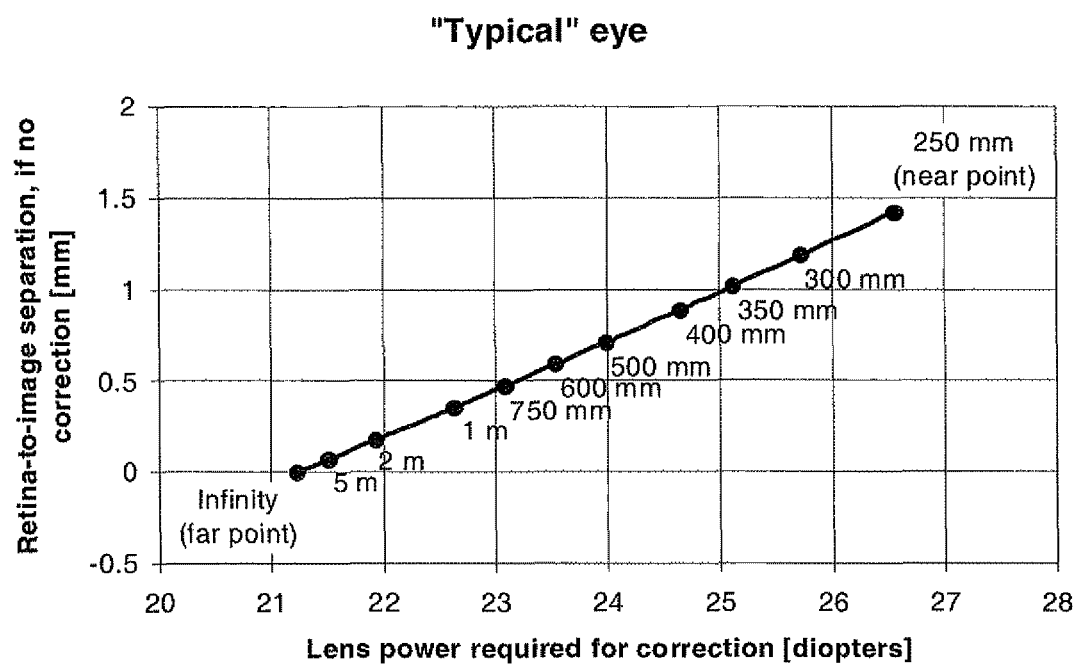
FIG. 4 is a plot of retina-to-image separation versus required lens power, for a variety of object distances, for the "typical eye" of FIG. 3.

The raytrace of FIG. 3 may also be used to predict the location of the image for a variety of object distances ("Z" in FIG. 2), and predict the power required of the intraocular lens to bring the objects into focus on the retina. FIG. 4 is a plot of retina-to-image separation versus required lens power, for a variety of object distances, for the "typical eye" of FIGS. 2 and 3. For an infinitely distant object, located at a "far point," (e.g., at or near optical infinity) the required lens power is 21.2 Diopters, and the image falls directly on the retina. As the object moves closer to the eye, we see an increase in the power required of the lens to bring the object into focus at the retina. For an object located 250 mm away from the spectacle (commonly denoted as the "near point," although other "near point" definitions may be used), the required lens power is about 26.5 Diopters, for an "accommodation range" of about 5.3 Diopters. Note that if the lens is well-corrected for "far vision," then a "near" object will have its image displaced about 1.4 mm behind the retina in this model. These numerical values are for a "typical" eye; individual eyes may vary from the "typical" values of FIG. 3. Although the numbers may vary, the trends are similar, with a higher lens power required at "near" focus than at "far" focus.

Note that because of the generally linear shape of the curve in FIG. 4, separations between the image and the retina may be expressed in terms of the equivalent power error.

For instance, if a lens is corrected for an infinite far point, then an object 1 meter away will form an image about 0.4 mm behind the retina. If the lens power were increased by 1.4 Diopters, then the object 1 meter away would be well-focused at the retina. The quantity typically used to describe this is "power error", which is usually expressed in Diopters. In other words, 1.4 Diopters of extra power is sufficient to bring a 1 meter-distant object into focus for a lens that is well-corrected for infinitely distant objects. Equivalently, if the lens is designed for 1 meter-distant objects, then decreasing the lens power by 1.4 Diopters is sufficient to bring infinitely-distant objects into focus.

Likewise, if a lens is corrected for the near point of 250 mm, then decreasing the lens power by 1.4 Diopters is sufficient to bring objects into focus at a distance of 350 mm. In general, it is more convenient to describe object distances by their corresponding power differences. For instance, without regard to sign, a "1.4 Diopter power error" may describe both a lens that is designed for infinitely distant objects and used at 1 meter, and a lens that is designed for 250 mm and used at 350 mm; both are "out of focus" by 1.4 Diopters. In many cases, the effects of defocus may be symmetric through-focus, so that a +1.4 Diopter error may have roughly the same performance as a −1.4 Diopter error. (Exceptions may include a non-zero spherical aberration, which is asymmetric through focus.)

We may summarize the findings of FIGS. 1 through 4 as follows: Defocus errors in the lens of an eye may be expressed in terms of equivalent power errors, in Diopters. A lens may be corrected for "far" objects, and may work sufficiently well in a +/− Diopter range around the "far point." Likewise, a lens may be corrected for "near" objects, and may work sufficiently well in a +/− Diopter range around "near." The term "work sufficiently well" is described in detail below.

One exemplary figure of merit for tracking the performance of visual systems is known as the "Modulation Transfer Function," or "MTF." MTF is particularly desirable as a figure of merit because it may be both predicted by simulation and approximately measured through the visual response of real patients.

The MTF is related to the apparent contrast of alternating bright and dark bars of an image. If the MTF is 1, then the bright areas appear completely bright, and the dark areas appear completely dark. If the MTF is 0, both areas appear as gray, with no distinction between bright and dark areas. Typically, MTF values lie between 0 and 1, with some light bleeding into the dark areas and some darkness bleeding into the light areas.

The MTF has a dependence on spatial frequency, which is inversely related to the width of the alternating bright and dark bars in the image. Note that MTF is particularly well-suited for human vision testing, in that the spatial frequency may be controlled during a test by controlling the size of a letter "E", where the widths of the prongs in the "E" have a prescribed size. Although MTF may be measured along two orthogonal axes, we assume rotational symmetry in this document.

Spatial frequency is typically reported in units of line pairs per mm at the retina. At low spatial frequencies (wide bars), the MTF is generally higher than at high spatial frequencies (narrow bars). For frequencies higher than a particular cutoff spatial frequency, the MTF is exactly 0; this is a property governed by the physics of diffraction.

The cutoff spatial frequency $SpFr_{cutoff}$ may be calculated for a round pupil, and is given by $$SpFr_{cutoff} = \frac{2r_{pupil}}{\lambda F},$$

where $r_{pupil}$ is the radius of the exit pupil of the lens, $\lambda$ is the wavelength, and F is the focal distance of the lens. For MTF calculations, we assume that the exit pupil of the lens and the principal planes of the lens are all coincident with the lens itself. For the "typical eye" lens of FIGS. 3 and 4, F is about 18.2 mm. We choose to evaluate the lens at a green wavelength of 550 nm. We also choose a lens diameter of 3 mm for the lens, so $r_{pupil}$=1.5 mm. This yields a cutoff spatial frequency of about 300 line pairs per mm. Note that this value is for incoherent light, as nearly everything seen with the eye is illuminated with incoherent light. Note that other wavelengths, distances and pupil sizes may be used as well; these numbers are merely exemplary and should not be construed as limiting in any way.

MTF may be calculated in a straightforward numerical manner, either by a raytracing program such as Oslo or Zemax, by another existing simulation tool, or by self-written code, all of which provide generally equivalent results with varying degrees of sophistication. For the plots in this document a self-written code was used, using a wavelength of 550 nm, a pupil radius of 1.5 mm, and a lens-to-retina separation of 18.2 mm. Note that other suitable values may be used for any or all of these quantities, including multiple wavelengths.

Figure 5:
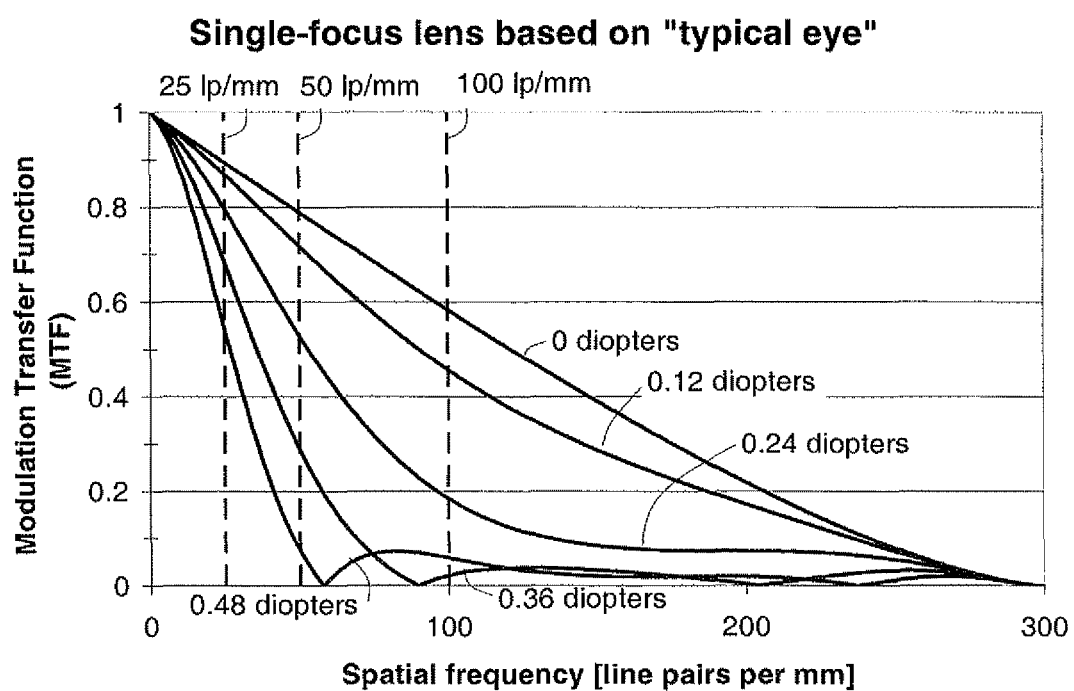
FIG. 5 is a plot of the MTF for the "typical eye" of FIGS. 3 and 4, for various amounts of defocus.

FIG. 5 is a plot of the MTF for the "typical eye" of FIGS. 3 and 4, for various amounts of defocus. The defocus is expressed in terms of power error, as described above.

At a spatial frequency of zero, the MTF is 1. At increasing spatial frequencies, the MTF decreases, not necessarily monotonically, until it reaches a value of 0 at the cutoff frequency of 300 line pairs per mm.

For no defocus, the MTF rolls off roughly linearly at low frequencies, then flattens out at high spatial frequencies. The value of this defocus-free MTF is known as the "diffraction limit," which represents a maximum attainable MTF for a particular spatial frequency. The actual values of the diffraction-limited MTF are given by the following equation:

$$MTF(SpFq) = \frac{2}{\pi}\left[\cos^{-1}\left(\frac{SpFq}{2SpFq_{cutoff}}\right) - \frac{SpFq}{2SpFq_{cutoff}}\sqrt{1 - \left(\frac{SpFq}{2SpFq_{cutoff}}\right)^2}\right],$$

where SpFq is the spatial frequency and $SpFq_{cutoff}$ is the (incoherent) spatial frequency cutoff, or about 300 lines pairs per mm (lp/mm, or mm$^{-1}$). This expression is valid only for a generally round pupil.

For non-zero defocus, the MTF decreases from the diffraction-limited MTF. For large enough defocus (see the 0.36 Diopter curve), the MTF reaches zero around 90 lp/mm; this results from the MTF being the magnitude of a complex quantity, the Optical Transfer Function, or OTF, which passes through zero.

The five curves in FIG. 5 may be compared with known MTF-versus-defocus plots for a round pupil. The curves for 0 D, 0.12 D, 0.24 D, 0.36 D and 0.48 D each correspond to wavefront errors ($W_{020}$) of 0 waves, 0.25 waves, 0.5 waves, 0.75 waves and 1 wave, respectively.

The conversion from power in Diopters to wavefront error in waves may be accomplished as follows. Consider the power perturbation $\Phi$. The lens is assumed to have an unperturbed focal distance of 18.2 mm, and a perturbed focal distance of $1/(\Phi+1/18.2$ mm$)$. Subtract the two, and rearrange to arrive at the axial distance $\Delta z$:

$$\Delta z = -\frac{\phi(18.2 \text{ mm})^2}{1 + \phi(18.2 \text{ mm})}$$

The wavefront error $W_{020}$ may be related to the axial distance $\Delta z$ by $$W_{020} = -\frac{r_{pupil}^2}{2\lambda(18.2 \text{ mm})^2}\Delta z.$$

For many optical systems involving human vision, the MTF values are reported at one or more representative spatial frequencies. For instance the performance of a system may be reported using the MTF at 25 lp/mm, the MTF at 50 lp/mm and/or the MTF at 100 lp/mm. Any or all of these may be used as a figure of merit, with higher values representing a "better" image.

Figure 6:
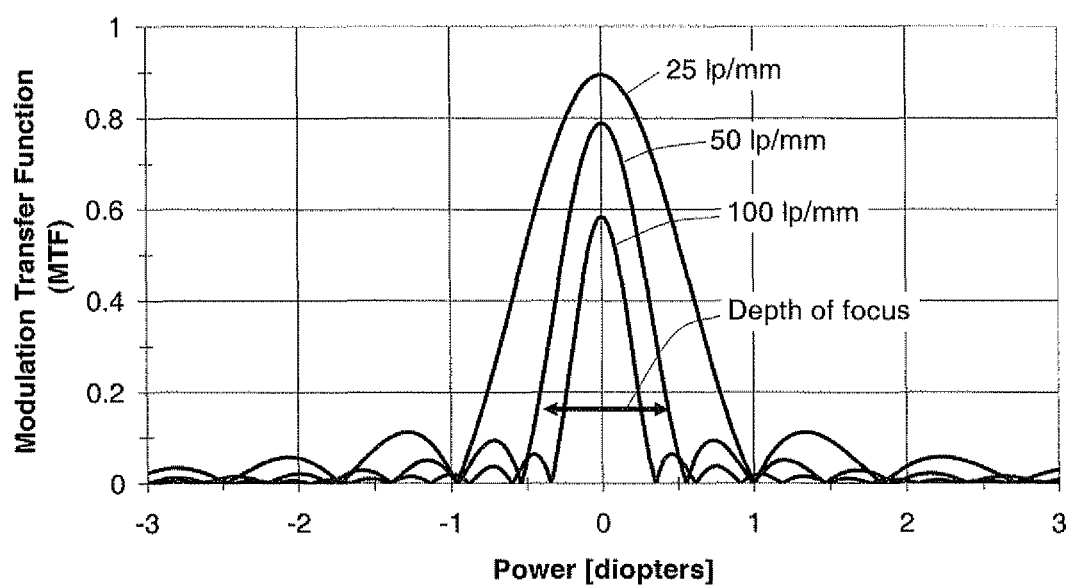
FIG. 6 is a plot of the MTF of the "typical eye" of FIGS. 3-5, versus defocus, at three representative spatial frequencies.

FIG. 6 is a plot of the MTF of the "typical eye" of FIGS. 3-5, versus defocus, at three representative spatial frequencies. The peak of the MTF curves is at zero defocus, and the peak values correspond to the intersections of the diffraction-limited curve of FIG. 5 with the three dotted lines. Because there are no other aberrations present, the MTF curves are symmetric through focus.

We may define a depth of focus for a lens based on any number of criteria, such as full-width-half-max (FWHM) of any of the MTF curves, a particular increase in spot size or wavefront error, a particular decrease in Strehl Ratio, or any other suitable criterion. For the illustrated embodiment, the depth of focus may be considered to be the focal range over which the MTF at 50 lines pairs per mm is greater than 0.17. In FIG. 6, the depth of focus is about 0.85 Diopters. As discussed in greater detail below herein, other criteria may be used to define a depth of focus.

Outside of the depth of focus, the MTF curve at 50 line pairs per mm drops to an unacceptably low value, meaning that an object at this particular spatial frequency would appear unacceptably blurred.

In practical terms, this means that if a single-focus intraocular lens, such as the intraocular lens 25 used in the "typical eye" of FIGS. 3-6, is designed for "far vision", it may not work for "near vision", which generally requires an add or accommodative power of about 3-6 Diopters. A patient with such a "far vision"-designed intraocular lens may see distant objects clearly, if the power error corresponding to the distance is within the depth of focus. Such a patient would likely require additional reading glasses or contact lenses to focus on near objects, and may require a second set of glasses for near or intermediate vision. This may be burdensome for the patient.

Fortunately, there exist multiple-focus intraocular lenses, which may form both a "near" and a "far" image on the retina simultaneously. After implantation, the patient's brain learns to concentrate on one image while ignoring the other. These lenses may produce two foci, each with its own depth of focus. The patient may be able to see "near" and "far" objects clearly, but may still require glasses to provide intermediate vision. This may be an improvement over a single-focus lens for the patient, and less burdensome for the patient. There is an ongoing effort to increase the depth of focus of both single and multi-focus intraocular lenses, to further reduce the dependence on spectacles for the patient.

Many of the multiple-focus intraocular lenses are constructed as follows. The anterior side and posterior side of the optic may each be convex, concave or planar. The optical powers from the anterior side and the posterior side add to form the refractive power of the lens. Typically, the refractive power of an intraocular lens may be in the range of about 5 Diopters to about 30 Diopters. Either or both of the anterior and posterior sides may have a multifocal diffractive or refractive element on it, for example in the form of concentric rings or zones. In the case of a diffractive multi-focal intraocular lens, the diffractive zones may have a phase structure in the form of local thickness variations along the surface of the diffractive element. For instance, "even"-numbered rings may be slightly more or less thick than "odd"-numbered rings, so that the transmitted optical path length is greater or less in the even rings than in the odd rings. Alternatively, the zones may each include a curved profile that affects the relative diffraction efficiency of particular diffraction orders. As a further alternative, an amplitude structure may be used, in which certain zones have a reduced or no intensity transmission, although this is inherently less efficient than a phase structure. There are two general classes of multifocal lenses, which may be similar in appearance and/or construction, but have slightly different characteristics. Both contain phase objects on one or both sides of the optic, typically in concentric rings or zones. For the purposes of this document, the phase object(s) may be referred to as a "diffractive element," for both classes discussed below.

The first class is known as "diffractive" multifocal, in which light transmitted through a radial zone may be roughly 180° out of phase (or out of phase by any other suitable value) with light transmitted through adjacent zones. In diffractive multifocal lenses, the radii that separate the zones are chosen for a particular desired power (or focal length), and are arranged in a prescribed manner based on the radius of the central zone. Light from a particular zone is not explicitly directed to one focus or the other; in other words, the diffractive element forms both foci by diffraction through the entire diffractive element. As a result, a diffractive multifocal intraocular lens may be constructed to near and far vision performance that is substantially the same for varying pupil sizes of the eye. Typically, diffractive multifocal lenses are bifocal in nature and, as a consequence, may not provide good intermediate vision. These "diffractive" multifocal lenses are shown and described in further detail below.

The second class is known as "refractive" multifocal, in which light from a particular zone is explicitly directed to one of two foci. For instance, the central (or $0^{th}$) zone may direct light to the "near" focus, the $1^{st}$ zone may direct light to the "far" focus, the $2^{nd}$ zone may direct light to the "near" focus, and so forth. The redirection of light is accomplished by including a radial refractive profile within each zone; this is in contrast with the "diffractive" elements, which may have a generally flat radial phase profile within each zone. The zone radii in a "refractive" element may be chosen arbitrarily, and may or may not coincide with those of a "diffractive" element. These are described further below. In the case of refractive multifocal intraocular lenses, various zones or annular regions of the optic surface may be constructed to particular foci. For example, some annular zones may be constructed to focus light onto the retina from a distant object or point source, while other zones are configured to focus light onto the retina from objects or point sources located at near or intermediate distances As a result, refractive multifocal intraocular lenses typically provide near and distant vision performance that varies with pupil size of the eye. Because each zone in a refractive multifocal intraocular lens may be directed to a specific focus, refractive multifocal intraocular lenses may be designed to provide at least some intermediate vision, in addition to near and distant vision.

The following text, as well as FIGS. 7 through 20, further describes "diffractive" multifocal lenses. However, it will be appreciated that embodiments of the invention may also include the use of refractive multifocal intraocular lenses.

Figure 7:
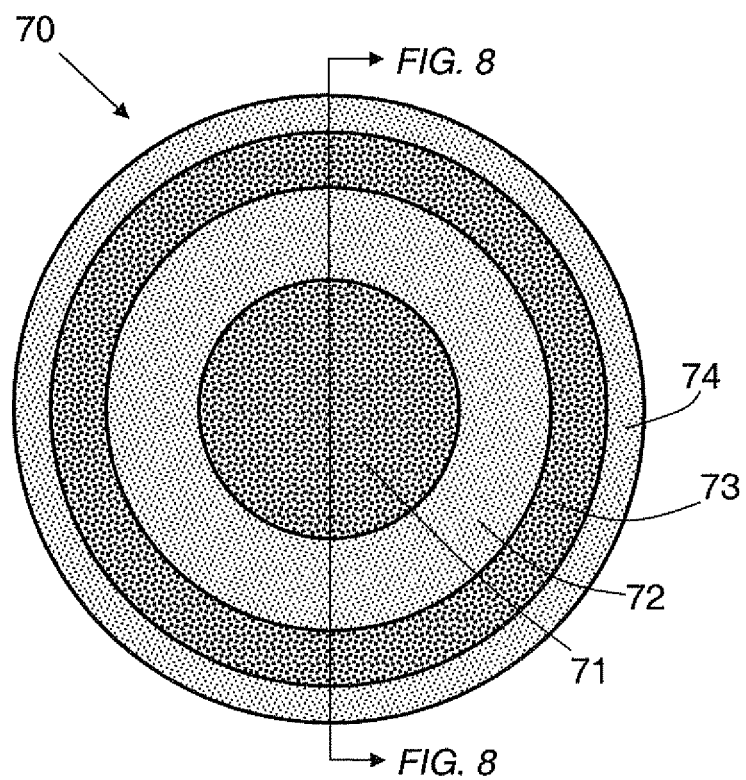
FIG. 7 is a front-view schematic drawing of a diffractive element.

FIG. 7 is a front-view schematic drawing of a diffractive element 70. Typically, the intraocular lens has refractive power from its two curved sides (or one curved side and one flat side), and additional diffractive power from the diffractive element 70. The diffractive element 70 may be located on one or both refractive sides of the optic; for the figures in this document, the diffractive element is shown as being on only one side, although in practice there may be diffractive portions on both sides.

FIG. 7 is a front-view plan drawing of a diffractive element 70. The diffractive element 70 includes a series of concentric rings or zones, with a central zone 71 and radially larger zones 71, 72, 73 and 74. Although four zones are pictured in FIG. 7, it will be understood that more or fewer zones may be used.

In the diffractive element 70, light transmitted through "even" zones 72 and 74 may be roughly 180° out of phase with light transmitted through "odd" zones 71 and 73. The terms "odd" and "even" are interchangeable herein, because there is no particular significance to the $0^{th}$ or $1^{st}$ zone. A numerical analysis of the zone radii follows below.

Figure 8:
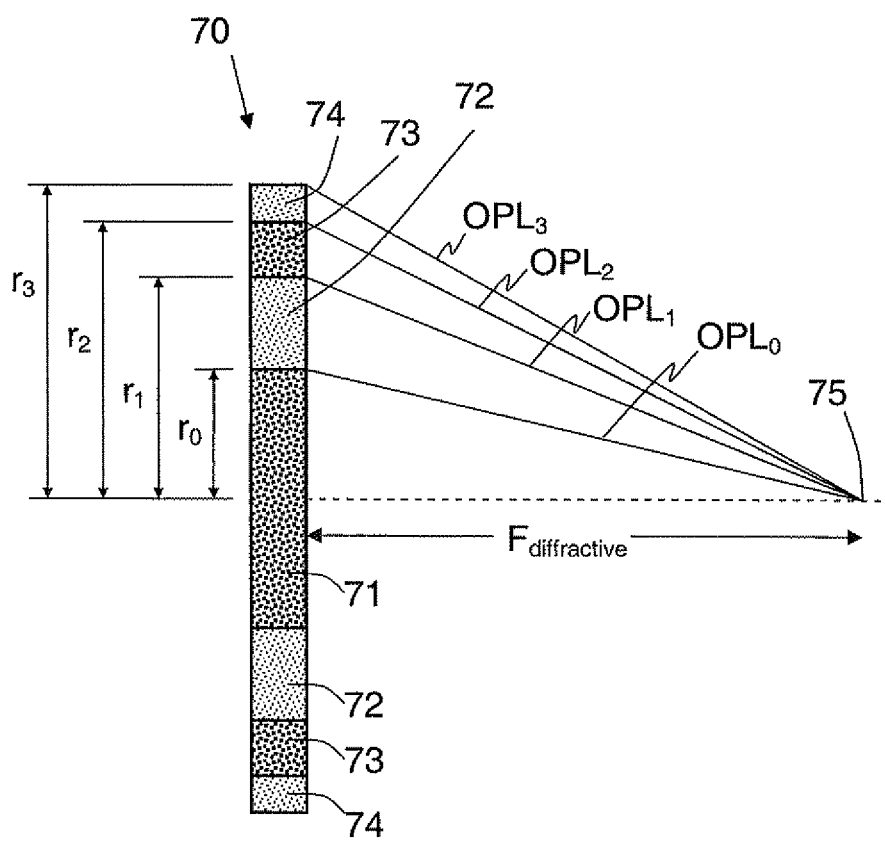
FIG. 8 is a radial cross-sectional drawing of the diffractive element of FIG. 7.

FIG. 8 is a radial cross-sectional drawing of the diffractive element 70 of FIG. 7. It will be understood that this diffractive element may be found along the curved surface of the optic, and that only the diffractive portion is shown in FIG. 8. The curved, refractive portion of the surface is not shown in FIG. 8.

The zones 71-74 are separated by various radii, denoted $r_0$ through $r_3$. The optical path lengths from these radii to a diffractive focus 75 are denoted as $OPL_0$ through $OPL_3$, respectively. Note that the separation between the diffractive element 70 and the diffractive focus 75, denoted as $F_{diffractive}$, is the focal length of the diffractive element if there were no refractive elements in the lens.

The relationships among the optical path lengths $OPL_i$ determine the radii $r_i$, as follows. To ensure that adjacent zones are out of phase, we require that $$OPL_{i+1} - OPL_i = \frac{\lambda}{2},$$

where $\lambda$ is the wavelength. We assume the diffractive element is essentially planar and write $$\sqrt{r_{i+1}^2 + F_{diffractive}^2} - \sqrt{r_i^2 + F_{diffractive}^2} = \frac{\lambda}{2}.$$

We assume that the radii $r_i$ are much smaller than the diffractive focal length $F_{diffractive}$, and rewrite to obtain $$r_i = \sqrt{i\lambda F_{diffractive} + r_0^2} = \sqrt{\frac{i\lambda}{\phi_{diffractive}} + r_0^2},$$

where the radius of the central zone $r_0$ may be chosen arbitrarily.

Note in the derivation above that the path length difference between adjacent radii is set to be $(\lambda/2)$. To ensure the condition that adjacent zones are out of phase, the optical path difference may alternatively be set to $\pm(\lambda/2)$, $\pm(3\lambda/2)$, $\pm(5\lambda/2)$, and so forth. These other path differences form the various diffracted orders from the diffraction element 70, with effective diffractive focal lengths of $\pm F_{diffractive}$, $\pm(F_{diffractive}/3)$, $\pm(F_{diffractive}/5)$, and so forth, and corresponding diffractive powers of $\pm\Phi_{diffractive}$, $\pm 3\Phi_{diffractive}$, $\pm 5\Phi_{diffractive}$, and so forth. It is interesting to note that these form only "odd" orders; there are no "even" orders from such a diffractive element.

Figure 9:
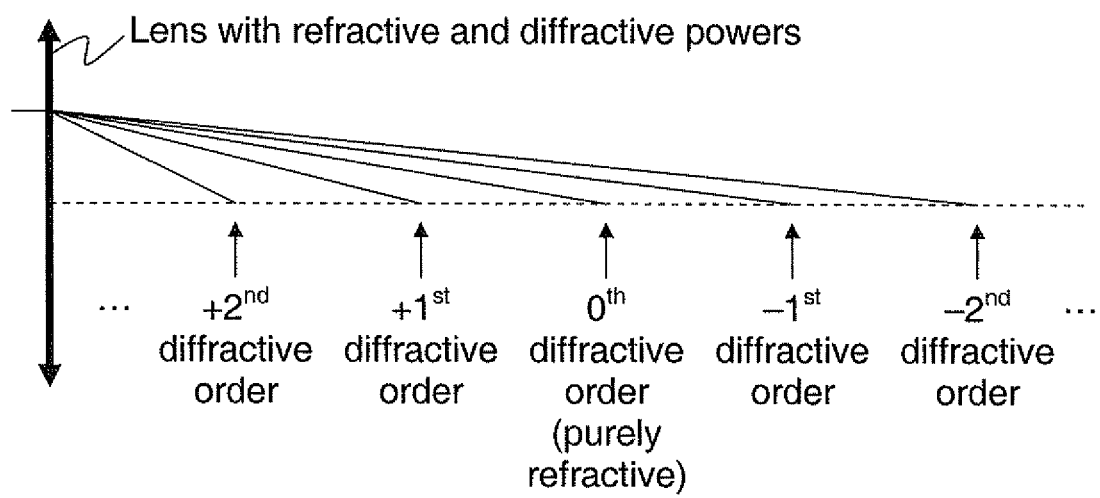
FIG. 9 is a schematic drawing of the diffracted orders from a lens having both refractive and diffractive powers.

FIG. 9 is a schematic drawing of the diffracted orders from a lens having both refractive (from the surface curvatures) and diffractive (from concentric zones in the diffractive element) powers. The zeroth order of the diffractive element is located at the refractive focus of the lens, as if the diffractive element were absent. The positive and negative orders may be evenly spaced, closer to and farther from the lens, respectively. It should be noted that there may be no light directed into the non-zero even diffracted orders, as discussed above.

Before considering some specific examples of diffractive elements, it is beneficial to digress momentarily to discuss diffraction efficiency. For the purposes of this document, the diffraction efficiency of each diffracted order is the percentage of incident power that is directed into each order. For a phase object, such as the diffraction elements considered herein, the sum of the diffraction efficiencies of all orders is generally 100%.

We now present the calculated diffraction efficiencies for a linear binary phase grating, which is similar in concept to the rotationally symmetric diffractive elements considered herein, but is mathematically simpler. The diffraction efficiency may be calculated analytically, as a function of duty cycle "dc" (which can vary from 0, where the width of the phase features is essentially zero, to 0.5, where the up/down phase features each have a width of half the pitch), peak-to-valley phase depth "pd" (which can vary from 0 to 360°, but the diffraction elements described herein have a peak-to-valley phase depth of 180°), and order number "n". The diffraction efficiency of the $0^{th}$ order is found to be $$4(dc)^2 \cos^2\left(\frac{pd}{2}\right).$$

The diffraction efficiency of the (non-zero)$\pm n^{th}$ order is $$\frac{4}{\pi^2} \frac{\sin^2(dc \times n \times 180°)}{n^2} \sin^2\left(\frac{pd}{2}\right).$$

For a duty cycle "dc" of 0.5 and a phase depth "pd" of 180°, the diffraction efficiency of both the $+1^{st}$ and $-1^{st}$ order is $(4/\pi^2)$, or about 40.53%. The remaining 18.94% of the light is divided among the remaining odd orders. The diffraction efficiency of the even orders is zero, including the $0^{th}$ order.

Although the radially symmetric diffraction elements of FIGS. 7 through 9 do not have the same calculated diffraction efficiencies as the linear binary phase grating, some general trends may apply. First, the diffraction efficiency into the positive orders may be equal to the diffraction efficiency into the negative orders. Specifically, for the diffractive elements considered herein, the $+1^{st}$ and $-1^{st}$ orders may have equal diffraction efficiencies. Second, the diffraction efficiency of the $0^{th}$ order may be 0, unless at least one of two conditions occur: (1) The phase depth difference between adjacent zones is shifted away from 180°, or (2) the duty cycle is shifted away from 50/50. In terms of the radially symmetric diffractive elements considered herein, the analogy to altering the duty cycle is varying the radius of the first ring. The analogous 50/50 condition is where the edge of the central zone is 180° out of phase with the center of the central zone. Mathematically, this occurs when $$r_0 = \sqrt{\lambda F_{diffractive} + \frac{\lambda^2}{4}}$$
$$\approx \sqrt{\lambda F_{diffractive}}$$
$$= \sqrt{\frac{\lambda}{\phi_{diffractive}}}.$$

For a wavelength of 550 nm and a power expressed in Diopters, the radius of the central zone, expressed in mm, simplifies to sqrt (0.55/Power). Some numerical examples follow: For a power of 1.5 Diopters, the radius of the central zone works out to 0.605 mm. For 1.0 Diopters, the central radius is 0.742 mm. For 0.5 Diopters, the central radius is 1.049 mm. Other powers may be used as well, such as 2 Diopters, 2.5 Diopters, 3 Diopters, and so forth.

When the central radius $r_0$ satisfies the above equation, the subsequent radii are calculated as described above, and the phase depth of adjacent zones is 180°, we expect that no light will be directed into the $0^{th}$ order, that about 40% of the light will be directed into the $-1^{st}$ order, that another 40% of the light will be directed into the $+1^{st}$ order, and that the remaining 20% of the light will be divided among the remaining odd orders. Several diffractive elements that satisfy these criteria are considered below, as well as several diffractive elements that explicitly violate these criteria.

Note that there may be some embodiments where more light is directed into one focus than into the other. For instance, rather than splitting the available light (roughly 80% of the total incident light) equally (50/50) into the near/far foci, the split may be 40/60, 60/40, 30/70, 70/30, or any other suitable ratio. In an extreme limit, the split may be 0/100 into the near/far, and the lens may be effectively monofocal.

FIGS. 10 through 20 describe various exemplary diffractive elements and their respective performances through-focus, when used as part of the "lens" in the "typical eye" described above. In all cases, each lens may be adapted to or designed for inclusion in a real patient's eye; the "typical eye" is merely exemplary and should not be construed as limiting in any way.

Figure 10:
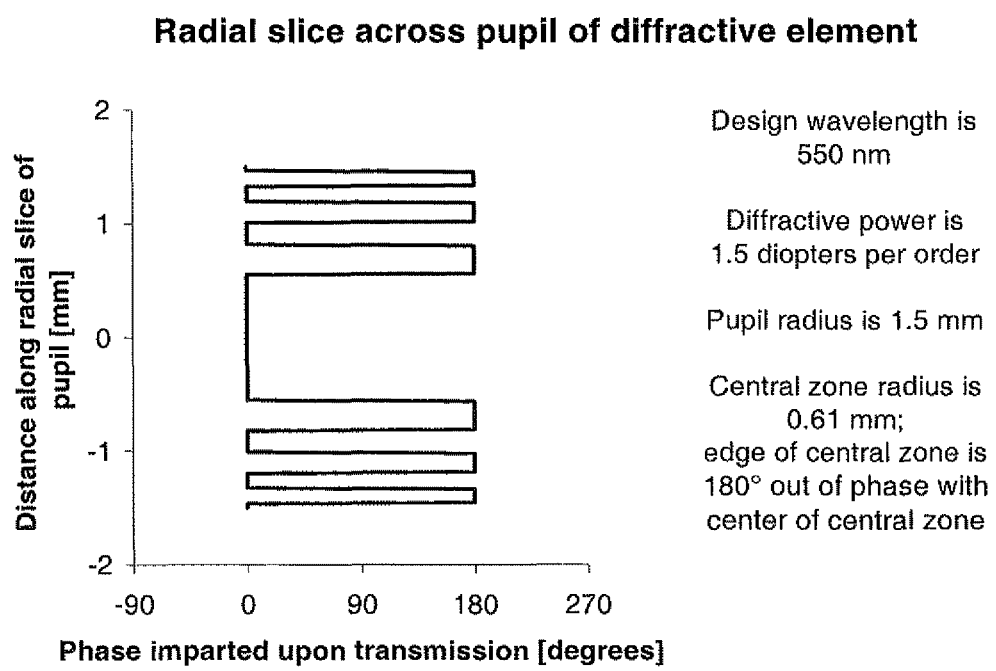
FIG. 10 is a cross-sectional slice of the phase imparted upon transmission through an exemplary diffractive element.

FIG. 10 is a cross-sectional slice of the phase imparted upon transmission through an exemplary diffractive element. Here, as with all of the diffractive elements considered in FIGS. 10 through 20, the design wavelength is 550 nm (in the green portion of the spectrum), and the pupil radius is 1.5 mm. These values are merely exemplary, and any suitable values for the design wavelength and pupil size may be used. Note that for the purposes of this document, the pupil size is the actual size of the diffractive element.

The diffractive power of the diffractive element of FIG. 10 is 1.5 Diopters per order. For instance, if the refractive power of the lens is 21.2 Diopters, then the plus first diffracted order has a combined (refractive+diffractive) power of 22.7 Diopters, the minus first diffracted order has a combined power of 19.7 Diopters, and so forth.

The radius of the central zone is 0.61 mm, which satisfies the condition described above, where most of the light is directed into the $+1^{st}$ and $-1^{st}$ orders, with very little in the $0^{th}$ order. We therefore choose a "near" focus to coincide with the $-1^{st}$ order and a "far" focus to coincide with the $+1^{st}$ order. In this lens, "near" and "far" zones are separated by 3 Diopters, which is a typical value for dual-focus intraocular lenses. The radii of the other zone edges in FIG. 10 are 0.86 mm, 1.05 mm, 1.21 mm, 1.35 mm and 1.48 mm.

Figure 11:
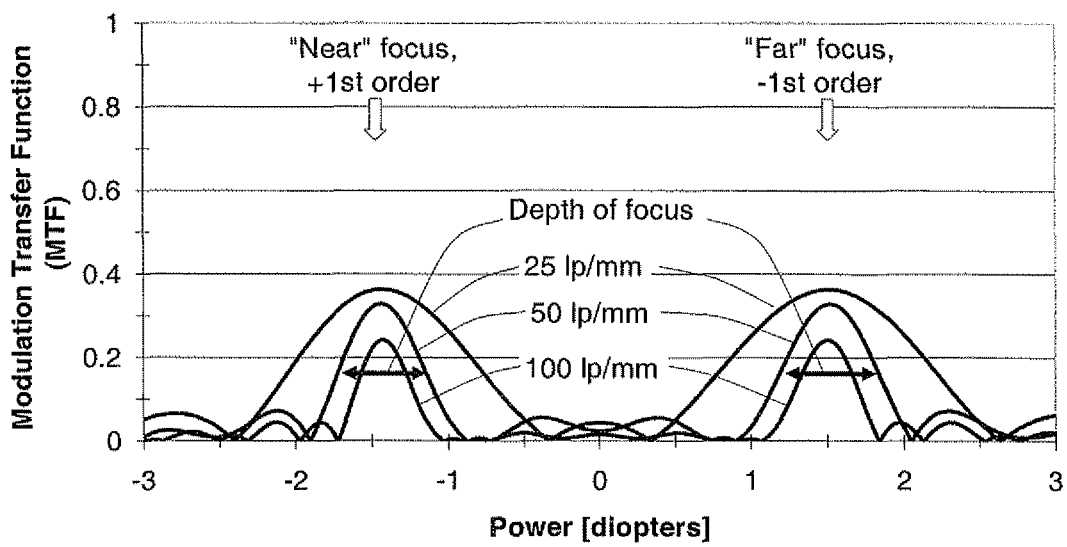
FIG. 11 is a through-focus plot of the MTF of the diffractive element of FIG. 10, at three representative spatial frequencies.

The through-focus performance of this diffractive element is shown in FIG. 11. The MTF curves for 25 lp/mm, 50 lp/mm and 100 lp/mm are all shown through-focus. (Recall that the horizontal axis is analogous to viewing objects at varying distances from the eye, with a "far" object by the left edge of the plot and a "near" object by the right edge of the plot.)

As expected, there are peaks at ±1.5 Diopters, which correspond to the $±1^{st}$ orders, and no peak at 0 Diopters, which corresponds to the $0^{th}$ order. For the definition of depth of focus used earlier, i.e., the region over which the MTF at 50 lp/mm is greater than 0.17, the depth of focus for each focus is about 0.6 Diopters.

In an attempt to increase the depth of focus beyond the two discrete peaks of FIG. 11, we may adjust the radius of the central zone. As shown earlier in the linear grating analogy, if we shift the duty cycle away from 50/50, the diffraction efficiency of the $0^{th}$ order increases from zero. For the diffraction element of FIG. 10, increasing the radius of the central zone beyond 0.61 mm has an analogous effect, diverting light from the $±1^{st}$ orders back into the $0^{th}$ order, thus potentially increasing the overall depth of focus (range over which the MTF at 50 lp/mm is greater than 0.17). The radii of other zones are calculated based on the desired power of the lens and the radius of the central zone, as described above.

Figure 12:
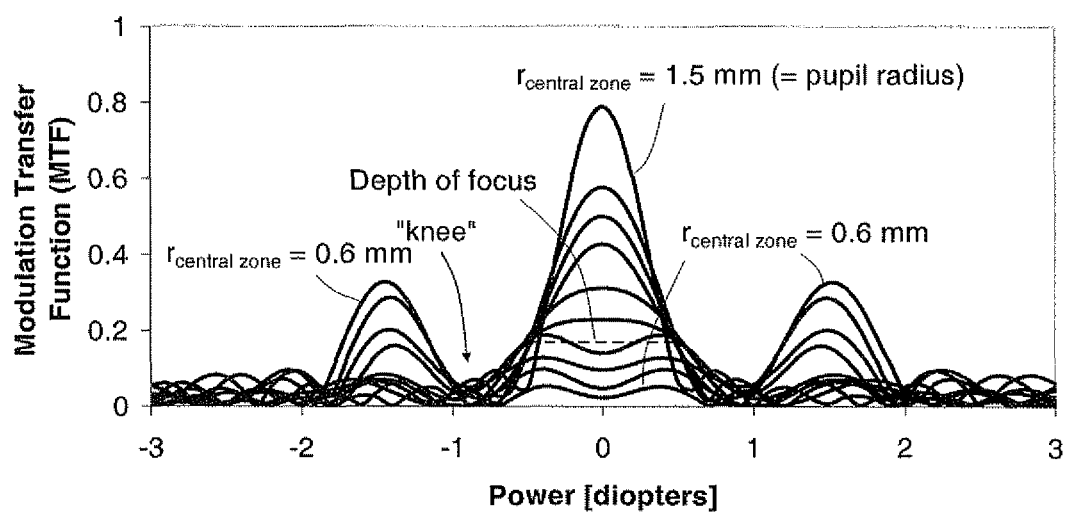
FIG. 12 is a through-focus plot of the MTF at 50 lp/mm of an exemplary diffractive element, for a variety of central zone radii.

FIG. 12 is a through-focus plot of the MTF at 50 lp/mm, for a variety of central zone radii. We see that as the central zone radius increases from 0.6 mm to 1.5 mm, the $±1^{st}$ order peaks disappear, and the $0^{th}$ order peak grows. While the $0^{th}$ order grows to have a depth of focus of about 1.0 Diopter, we lose the effects of the $±1^{st}$ orders, each of which does not have a depth of focus substantially greater than the 0.6 Diopters shown in FIG. 11.

In particular, note that as the central zone radius is varied over its range, the MTF plots form a "knee," which may be thought of as follows. For all the MTF curves in FIG. 12, we define a function as the maximum value of all the MTF curves, over the whole x-axis. The "knee" may be thought of as a local minimum of this function. We see a "knee" at roughly 1.0 Diopters and an MTF value of around 0.08, and a corresponding knee at −1.0 Diopters and an MTF of around 0.08. This knee falls below the depth of focus threshold MTF value of 0.17. Thus, changing the size of the central zone does not appear to provide a significant increase in overall depth of focus.

Figure 13:
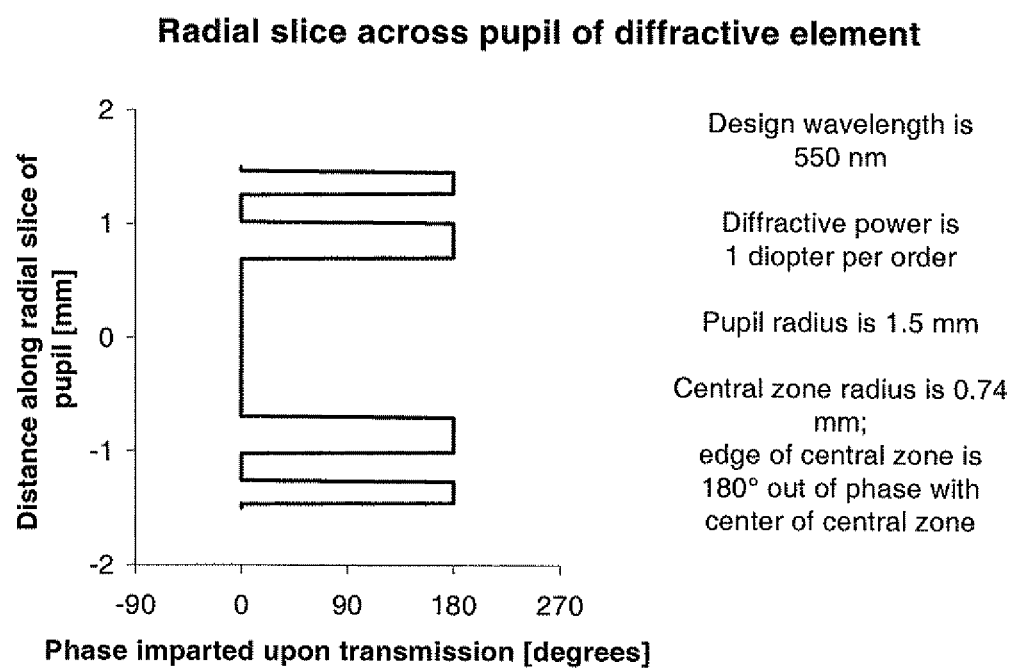
FIG. 13 is a cross-sectional slice of the phase imparted upon transmission through an exemplary diffractive element.

Another parameter that may be used in attempting to increase the depth of focus is reducing the diffractive power of the diffractive element so that the $+1^{st}$ and $-1^{st}$ orders are closer to each other. Referring to FIG. 13, a diffractive lens is illustrated that has a diffractive power of 1 Diopter per order. The central zone radius is chosen in accordance with the duty cycle condition described above, and is 0.74 mm. The radii of the larger concentric zones are calculated as described above, and are 1.05 mm, 1.28 mm and 1.48 mm.

Figure 14:
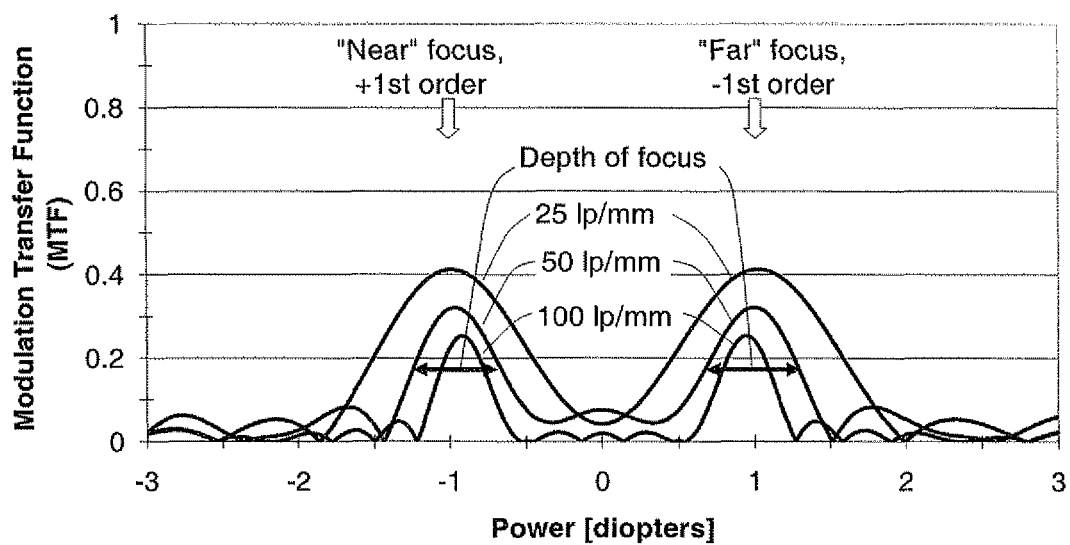
FIG. 14 is a through-focus plot of the MTF of the diffractive element of FIG. 10, at three representative spatial frequencies.

The performance of the diffractive element of FIG. 13 is shown in FIG. 14. Compared with FIG. 13, the "near" and "far" foci are moved toward each other, but the depth of focus for each is still about 0.6 Diopters. This value may not be a significant improvement over the depth of focus shown in the plots of FIG. 11. Simply moving the "near" and "far" foci closer together by reducing the power of the diffractive element, without doing anything else, does not seem to substantially increase the depth of focus.

Figure 15:
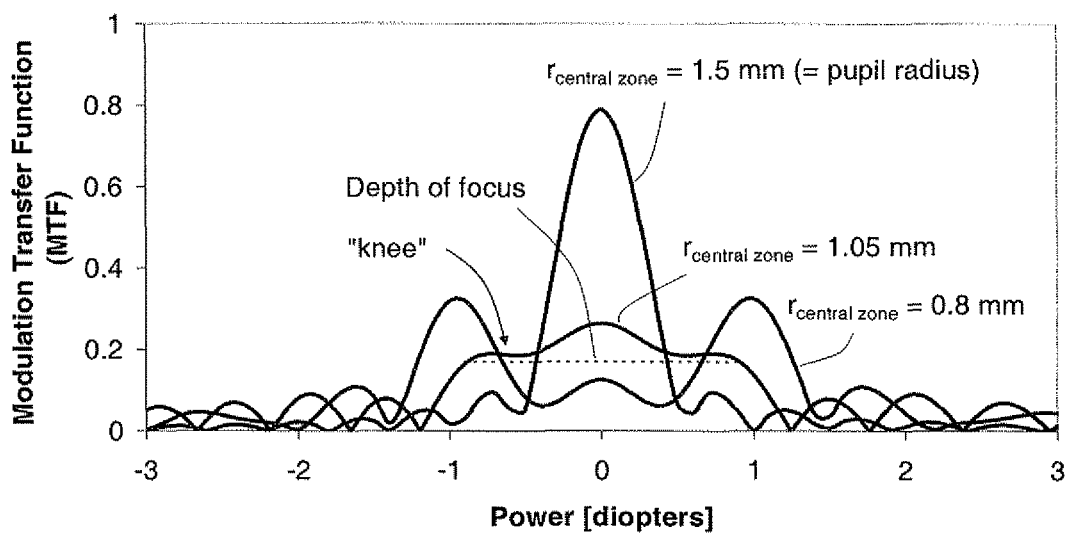
FIG. 15 is a through-focus plot of the MTF at 50 lp/mm of an exemplary diffractive element, for a variety of central zone radii.

If we then take the diffractive element of FIG. 13, and increase the central zone radius beyond 0.74 mm, and plot the through-focus MTF at 50 lp/mm, we arrive at the curves of FIG. 15. These curves also show a "knee" at about 0.6 Diopters and an MTF value of about 0.2, and a corresponding "knee" at −0.6 Diopters and an MTF of 0.2. In contrast with the curves of FIG. 12, it may be noted that this knee is above the MTF threshold of 0.17 that defines the depth of focus. As the central zone radius is increased, the $±1^{st}$ order peaks shrink and the $0^{th}$ order peak grows, but there is a range of central zone radii at which the peaks all blend together, so that the overall depth of focus may be significantly increased.

The curves of FIG. 15 show that adjusting the central zone radius (and therefore adjusting the diffraction efficiency into the $0^{th}$ order) may have an effect on the depth of focus.

For a small central zone (r=0.8 mm), most of the light is directed into the $+1^{st}$ and $-1^{st}$ orders, with little remaining in the $0^{th}$ order. As a result, we see two distinct peaks, separated by a region in which the MTF is lower than the threshold of 0.17. The depth of focus may not be significantly increased due to these two separated peaks.

For a large central zone (r=1.5 mm), most of the light is directed into the $0^{th}$ order, with little or none reaching the $+1^{st}$ and $-1^{st}$ orders. This is essentially the same case as a single-focus lens with no diffractive effects. The depth of focus, therefore, is not significantly increased beyond the single-focus case.

For a properly-sized central zone (r=1.05 mm), the overall depth of focus may be increased by directing some light into all of the $-1^{st}$, $0^{th}$ and $+1^{st}$ orders. The peak MTF is reduced from the single-focus case, however the width is increased over the single-focus case. This may be considered an extended depth focus. We examine the case of the properly-sized central zone in more detail in FIGS. 16 and 17.

Figure 16:
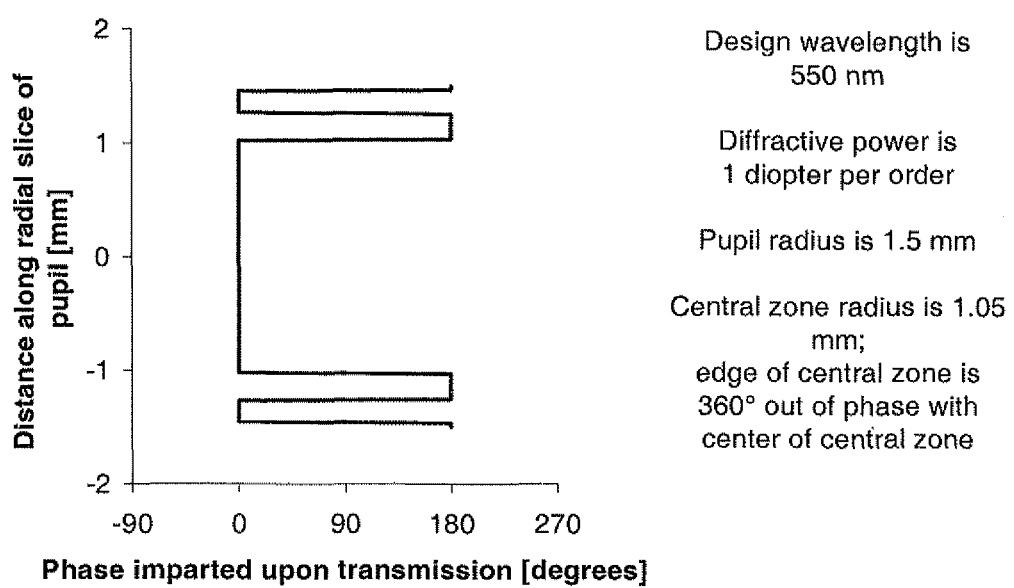
FIG. 16 is a cross-sectional slice of the phase imparted upon transmission through an exemplary diffractive element.

A 1-Diopter diffractive element, similar to FIG. 13 but having a central zone radius of 1.05 mm, is shown in FIG. 16. The subsequent zone radii are calculated as described above, and are 1.28 mm and 1.48 mm. For a central zone radius of 1.05 mm, the edge of the central zone is 360° out of phase with the center of the central zone, compared to 180° for the element of FIG. 13.

Figure 17:
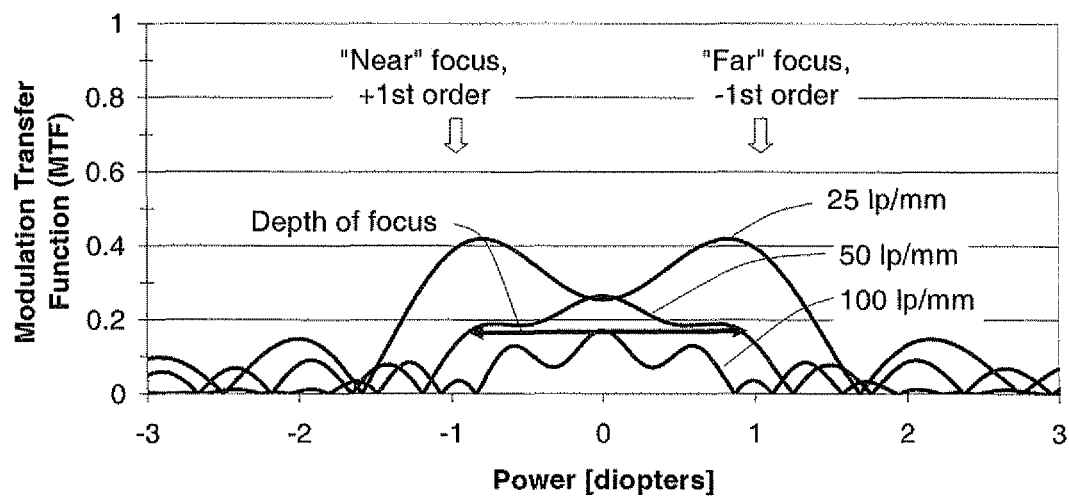
FIG. 17 is a through-focus plot of the MTF of the diffractive element of FIG. 10, at three representative spatial frequencies.

FIG. 17 shows the through-focus performance of the element of FIG. 16. Here, the depth of focus is about 1.8 Diopters, which is roughly three times the depth of focus of any single focus of FIGS. 10-14. In addition, the total range over which the MTF at 50 lp/mm is above a threshold value of 0.17 is approximately 1.5 times greater than that for both foci combined in FIGS. 10-14. The MTFs at 25 lp/mm and 100 lp/mm are shown in FIG. 17 along with the MTF at 50 lp/mm. All three MTF curves are well-behaved within the depth of focus, with none falling to zero in this range.

Figure 18:
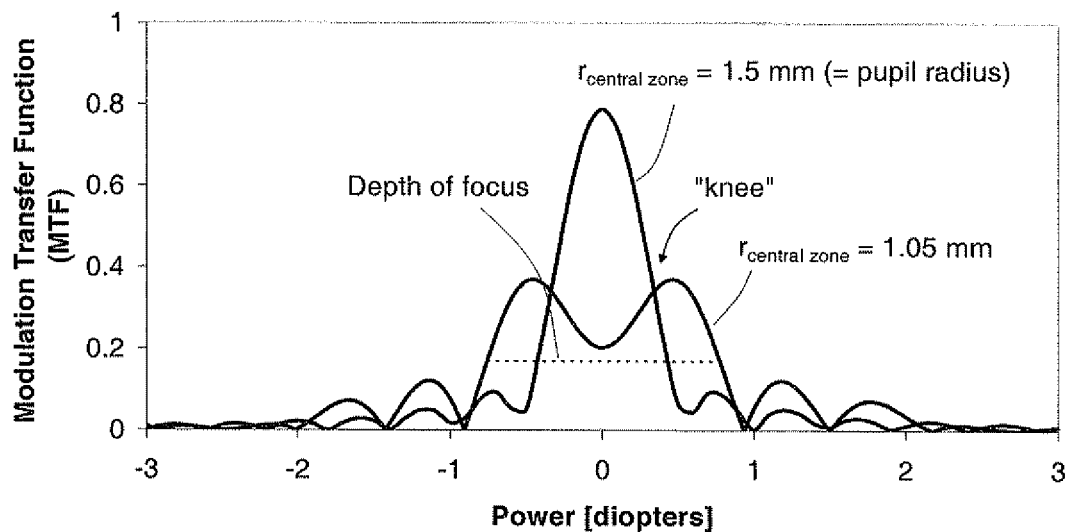
FIG. 18 is a through-focus plot of the MTF at 50 lp/mm of an exemplary diffractive element, for two central zone radii.

FIG. 18 is a through-focus plot of MTF at 50 line pairs per mm, for a diffractive element with 0.5 Diopters per order, for a variety of central zone radii. The remaining zone radii are calculated as described above. This plot is analogous to FIG. 15 (1 Diopter per order) and FIG. 12 (1.5 Diopters per order). The so-called "knee" of the curves in FIG. 18 occurs at about ±0.4 Diopters and an MTF of about 0.4. Here, the knee is well above the MTF threshold used to define the depth of focus.

Figure 19:
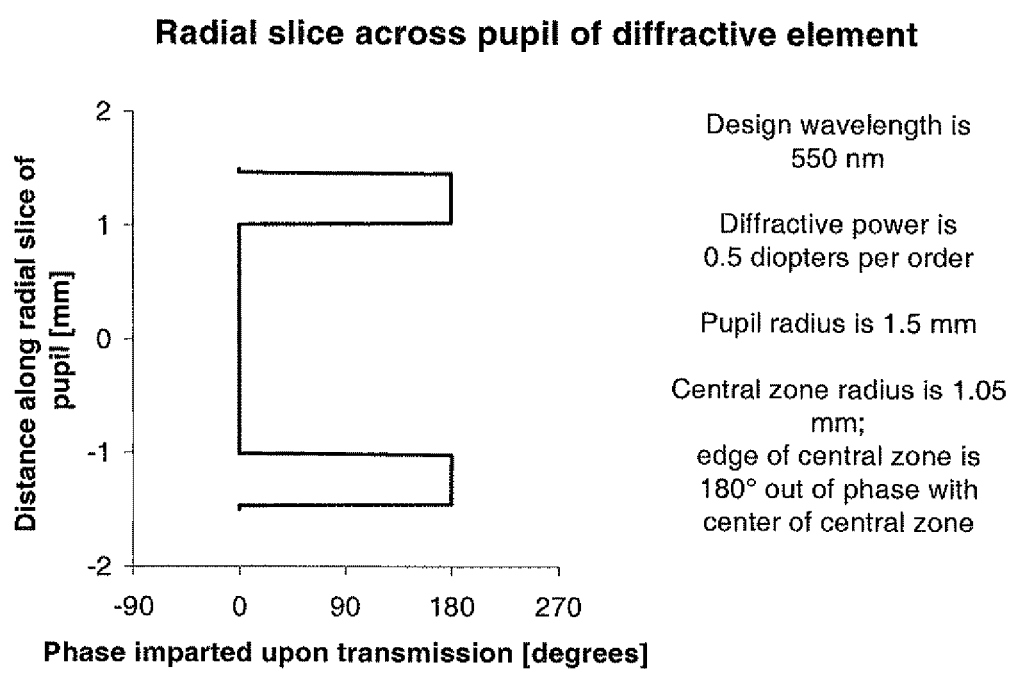
FIG. 19 is a cross-sectional slice of the phase imparted upon transmission through an exemplary diffractive element.

FIG. 19 illustrates a diffractive lens corresponding to the curve in FIG. 18 in which the central zone has a radius of 1.05 mm. The edge of the central zone is 180° out of phase with the center of the central zone; this is analogous in construction with the diffractive elements shown in FIG. 13 (1 Diopter per order) and FIG. 10 (1.5 Diopters per order). The other zone radius is calculated as described above, and is 1.48 mm. Note that because the pupil radius is 1.5 mm, that there is effectively only one additional zone beyond the central zone.

Figure 20:
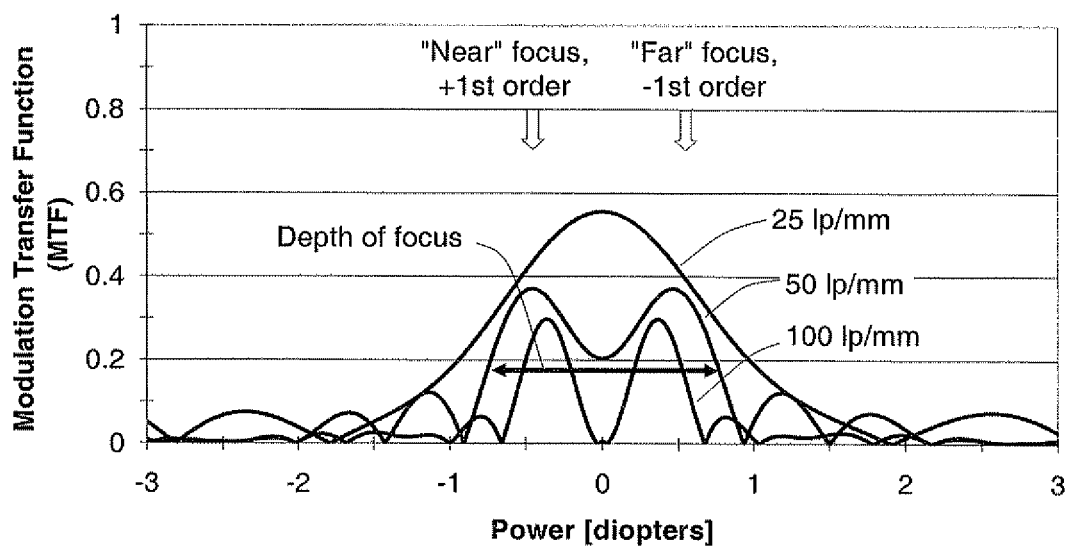
FIG. 20 is a through-focus plot of the MTF of the diffractive element of FIG. 10, at three representative spatial frequencies.

FIG. 20 shows the through-focus performance of the diffractive element of FIG. 19. The depth of focus, defined as the region over which the MTF at 50 lp/mm is greater than 0.17, is about 1.5 Diopters. However, the MTF at 100 lp/mm drops to zero near the center of this focus range, which may be undesirable in some circumstances. For instance, in some embodiments it may be a desirable characteristic that the MTF values be positive within the depth of focus, out to a particular spatial frequency, such as 100 lp/mm or any other suitable value. However, in some cases, it may be acceptable to have an MTF drop to zero at a particular spatial frequency.

Note that there may be other features present in the diffractive zones, in addition to or in place of a uniform phase object. For instance, there may be a radial phase feature known as a "blaze", analogous to the uniform "slant" of the phase in a linear blazed grating, which can direct light preferentially into one or more diffracted orders. For example, a blaze profile may have a dependence on r squared, where r is the distance from the optical axis. The blaze may extend over the entire diffractive element, or may be present in only select radial zones.

Much of the above analysis is applicable to such blazed diffractive lenses, only using different diffracted orders from the $+1^{st}$ and $-1^{st}$ orders shown in FIGS. 10 through 20. For instance, the power may be split between the $0^{th}$ and $+1^{st}$ orders, the $+1^{st}$ and $+2^{nd}$ orders, the $+2^{nd}$ and $+3^{rd}$ orders, or the $+3^{rd}$ and $+4^{th}$ orders, and so forth. Using specific, predetermined orders other than the $+1^{st}$ and $-1^{st}$ orders may be beneficial in some embodiments, and may have advantages in certain circumstances. For instance, correction for chromatic aberration may be possible and/or easier for certain combinations of orders. Examples of such designs are found in U.S. Pat. Nos. 5,144,483; 4,655,565; 5,748,282; or 5,229,797, all of which are herein incorporated by reference in their entirety.

Note also that the term "adjacent" orders may refer to consecutive orders as defined above, such as the $0^{th}$ and $+1^{st}$ orders, the $0^{th}$ order and $-1^{st}$ orders, the $+3^{rd}$ and $+4^{th}$ orders, the $-3^{rd}$ and $-4^{th}$ orders, and so forth. Alternatively, the term "adjacent" orders may refer to consecutive orders that have a non-zero diffraction efficiency or have a diffraction efficiency that is substantially greater than zero (e.g., greater than 2% or greater than 5%) at a design wavelength or over a predetermined range of wavelengths; recall above that in some cases the non-zero even diffracted orders may have a diffraction efficiency of zero, or substantially zero, at a design wavelength or over a predetermined range of wavelengths. In these cases, the diffracted orders may be renumbered so that both even and odd orders may have non-zero diffraction efficiencies. Here, "adjacent" orders may refer to these renumbered orders.

In at least some of the above examples, an extended depth of focus was produced using diffractive lenses comprising zones of constant phase that produced significant energy in at least two diffraction orders. As used herein, the term "extended depth of focus" means a depth of focus that exceeds that of a similar spherical intraocular lens comprising opposing spherical surfaces and having substantially the same optical power as an optical power of the lens with the extended depth of focus. In the above examples, the extended depth of focus was produced by using a combination of a relatively low add power (as compared to a traditional diffractive, multifocal intraocular lens) and predetermined radius for a central zone. Such extended depth of focus performance is illustrated at least in FIG. 15 (for a central zone radius of 1.05 mm), FIG. 17 (at least at a frequency of 50 lp/mm), FIG. 18 (for a central radius of 1.05 mm), and FIG. 20 (at least at a frequency of 50 lp/mm).

Note also that intraocular lenses according to embodiments of the invention may use additional techniques to extend the depth of focus, in addition to those described above herein (e.g., the use of diffractive lenses with low add powers of about 2 Diopters (FIG. 16) or about 1 Diopter (FIG. 19)). For instance, in some embodiments, a refractive power and/or base curvature profile(s) of an intraocular lens surface(s) may contain additional aspheric terms or an additional conic constant, which may generate a deliberate amount of spherical aberration, rather than correct for spherical aberration. In this manner, light from an object that passes through the cornea and the lens may have a non-zero spherical aberration. Because spherical aberration and defocus are related aberrations, having fourth-order and second-order dependence on radial pupil coordinate, respectively, introduction of one may be used to affect the other. Such aspheric surface may be used to allow the separation between diffraction orders to be modified as compared to when only spherical refractive surfaces and/or spherical diffractive base curvatures are used. An additional number of focus-extending techniques are described in detail in U.S. Pat. No. 7,061,693, titled "Optical method and system for extended depth of focus," issued on Jun. 13, 2006 to Zalevsky, and incorporated by reference in its entirety herein. In some embodiments, a refractive lens may include one or more surfaces having a pattern of surface deviations that are superimposed on a base curvature (either spherical or aspheric). Examples of such lenses, which may be adapted to provide lenses according to embodiments of the present invention, are disclosed in U.S. Pat. No. 6,126,286 and U.S. Pat. No. 6,923,539 and U.S. Patent Application No. 2006/0116763, all of which are herein incorporated by reference in their entirety.

Referring to FIGS. 21A and 21B, in certain embodiments of the present invention, an ophthalmic lens 200 comprises an optic 210 that includes an anterior surface 220 having a first shape 222 and an opposing posterior surface 230 having a second shape 232, the first and second shapes 222, 232 providing a refractive power. The optic 210 further comprises a diffractive element or pattern 240 imposed on, added to, or combined with the second shape 232. The first and second surfaces 220, 230 together provide a base power and an add power, the add power generally being less than or equal to about two Diopters or even less or equal to about one Diopter, depending on the desired performance of the optic 210 (e.g., the range of the depth of focus under certain conditions, the number of distinct foci desired under certain conditions, the range of vision desired under certain conditions, and the like).

The optic 210 has a clear aperture through which light from an object is transmitted through the anterior and posterior surfaces 220, 230 to form an image on the retina of a subject or patient. As used herein the term "clear aperture" means the portion of an optic that limits the extent of the rays from an object that contribute to the corresponding or conjugate image. The "clear aperture" is generally express as a diameter of a circle.

In the illustrated embodiment, the diffractive pattern 240 includes a blazed radial profile. Alternatively, a binary phase grating may be used, for example, as discussed above with regards to FIGS. 10-20. It is instructive to compare an exemplary lens having a diffractive pattern (referred to below as "extended focus") with a similar intraocular lens that lacks such a diffractive pattern (referred to below as "refractive").

The surfaces 220 and/or 230 of the optic 210 may be purely refractive and have a shape or profile that is either spherical or aspheric. The shape of the surface may be represented by sag Z given by the following equation:

$$Z(r) = \frac{r^2/R}{1 + \sqrt{1 - r^2(CC+1)/R^2}} + ADr^4 + AEr^6$$

where r is a radial distance from the center or optical axis of the lens, R is the curvature at the center of the lens, CC is the so-called conic constant, and AD and AE are polynomial coefficients additional to the conic constant CC.

In the illustrated embodiment, the diffractive pattern 240 has a relatively low add power and is imposed on second shape 232. The combination of the diffractive pattern 240 and the second shape define the overall form of the posterior surface 230. The resulting optic 210, illustrated in FIG. 21B, provides an increased depth of focus when illuminated at a predetermined wavelength, or range of wavelengths, relative to a reference optic without the diffractive pattern 240 and having a refractive power that is substantially equal to a base power.

Note that the diffraction element or pattern 240 may be imposed on, added to, or combined with the first shape 222 or diffractive patterns may be imposed on both shapes 222, 232. Note also that the optic may be bi-convex, as drawn in FIG. 21, or may optionally be plano-convex or meniscus. For the purposes of comparison between "spherical" and "extended focus" lenses, the exemplary optic 210 is assumed to be bi-convex and symmetric (having the same radius of curvature), with the diffractive pattern 240 being added to the second shape 232 for provide the posterior surface 230 of a simulated "refractive" lens to form a simulated "extended focus" lens. The simulations may be performed using, for example, ray tracing or lens design software such as Oslo, Zemax, Code V, or any other suitable program.

The following two sections provide two different simulated comparisons of an "extended focus" lens with a "refractive" lens. The first comparison uses an anatomically accurate model of the surfaces in the eye. The second uses an eye model that can also be used to measure a real lens in a physical laboratory instrument, in addition to being simulated. Both are described in greater detail below.

The first simulated comparison uses a model eye based on an article by H. L. Liou, and N. A. Brennan, "Anatomically accurate, finite model eye for optical modeling," J Opt Soc Am A, 14(8), 1684-1695. The Liou-Brennan model eye uses distances and curvatures that correspond to those in an average-shaped, average-sized eye.

Figure 22:
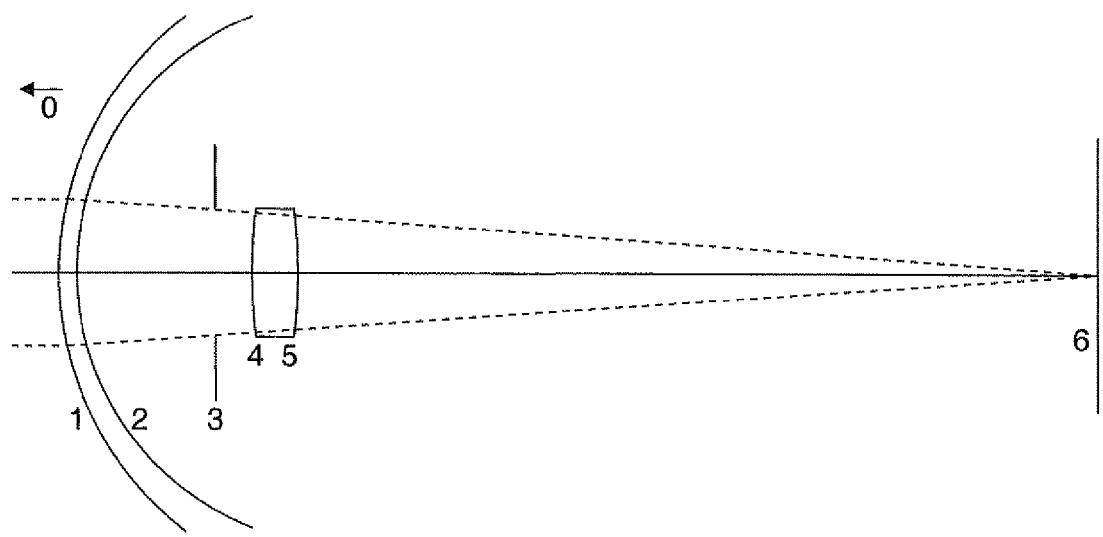
FIG. 22 is a surface-by-surface schematic drawing of a Liou-Brennan model eye with the intraocular lens of FIG. 21.

FIG. 22 is a surface-by-surface schematic drawing of the simulated eye systems for the Liou-Brennan model. The dotted lines in FIG. 22 represent rays from an infinitely distant object, passing through the zeroth order of the diffractive element and forming a "far" focus at the retina. There are six surfaces in the simulated Liou-Brennan eye, with a number 0 surface located infinitely far away. Each surface is described below.

Surface 0 may be considered to be the object of the system. Surface 0 is infinitely far away, or any suitable approximation of infinity, such as 1e9 mm or 1e20 mm. The material after surface zero is air, with a refractive index of 1.

Surface 1 is the anterior surface of the cornea, with a radius of curvature of +7.77 mm and a conic constant (also known as "asphericity") of −0.18.

The refractive index between surface 1 and surface 2 is the refractive index of the cornea, with a value of about 1.376 at a wavelength of 555 nm. The separation between surface 1 and surface 2 is the thickness of the cornea, 0.5 mm.

Surface 2 is the posterior surface of the cornea, with a radius of curvature of −6.4 mm and a conic constant of −0.6.

The refractive index between surface 2 and surface 3 is the refractive index of the aqueous humor, with a value of about 1.336 at a wavelength of 555 nm. The separation between surface 2 and surface 3 is 3.16 mm.

Surface 3 is the iris of the eye, and is the aperture stop of the simulated optical system. It has a radius proportional to the pupil diameter, and has no power or curvature. The pupil diameter in the simulations is 3 mm.

The refractive index between surface 3 and surface 4 is the refractive index of the aqueous humor, with a value of about 1.336 at a wavelength of 555 nm. The separation between surface 3 and surface 4 is 0.5 mm.

Surface 4 is the anterior surface of the intraocular lens, with a radius of curvature of +12.154 mm.

The refractive index between surface 4 and surface 5 is the refractive index of the intraocular lens. The lens is made of a silicone material, with a value of about 1.459 at a wavelength of 555 nm. The separation between surface 4 and surface 5 is the axial thickness (or "center thickness") of the lens, 1 mm.

Surface 5 is the posterior surface of the intraocular lens, with a radius of curvature of −12.154 mm. Note that the lens is bi-convex and symmetrical, with a conic constant of 0 and no aspheric terms. In other words, the shape of the anterior and posterior surfaces is spherical. Alternatively, the anterior and/or posterior surfaces of the lens may include a non-zero conic constant or one or more aspheric terms.

For the "refractive" lens used as a benchmark in this comparison, the optic includes surfaces 4 and 5 as described above. For the "extended focus" lens, surface 5 also includes a parabolic, blazed diffractive profile, imposed on the shape of the surface.

The blazed profile may be described by equations equal to or similar to those described in the article by A. L. Cohen, "Practical design of a bifocal hologram contact lens or intraocular lens," Applied Optics, 31 (19), 3750-3754 (1992). The diffractive element uses the $0^{th}$ and $+1^{st}$ diffracted orders. The radius of the first ring in the diffractive profile is 0.95 mm, corresponding to an add power of 1.2 Diopters. The depth of the profile is 3.2 microns, which converts to a phase imparted upon transmission of (3.2 microns times (1.459-1.336) divided by 0.555 microns), or about 0.7 wavelengths, or about 255 degrees of phase. The parabolic profile extends across all zones, with a step discontinuity at the edge of each zone. The step height may be varied from 3.2 microns, depending on the refractive index of the lens material or other design factors. The step height will generally be between about 1 micron and about 3 microns, preferably between about 1.5 microns and about 2.0 microns.

The refractive index between surface 5 and surface 6 is the refractive index of the vitreous humor. In this model, the refractive index of the vitreous humor is taken to be the same as the aqueous humor, or about 1.336 at a wavelength of 555 nm. The separation between surface 5 and surface 6 may be set to a "solve" in a raytrace program, such as OSLO or ZEMAX, and is about 18.7 mm.

Surface 6 is the retina, and is the image plane for the simulated optical system.

The eye model with the above intraocular lens was evaluated in polychromatic light, as described in the Liou-Brennan reference. Typically, the simulations may be performed with a primary wavelength of 555 nm, and a weighting for the other wavelengths in accord with the spectral response of the eye. In other embodiments, the performance of the lens may be modeled and/or evaluated with other weighting factors, for example, to account for varying lighting conditions and/or to account for differences between scotopic and photopic vision. Alternatively, the lens may be modeled and/or evaluated at a plurality of two or three wavelengths representative of the visible range or a particular lighting condition, or at a single wavelength representative of the visible range or a particular lighting condition (e.g., at a wavelength of 550 nm).

Figure 21:
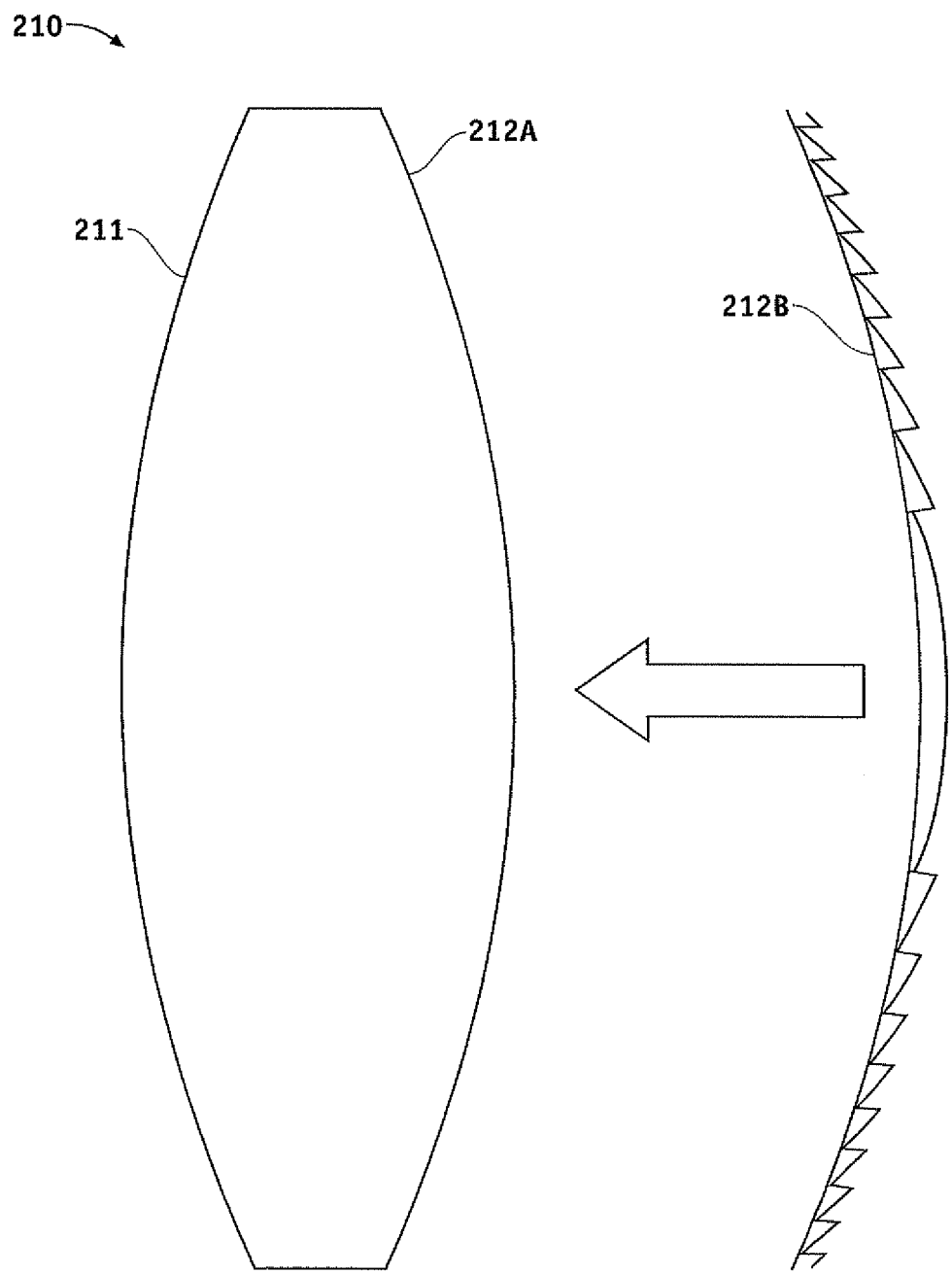
FIG. 21A, B are cross-sectional drawings of an exemplary intraocular lens, both with and without a diffractive element.
Figure 23:
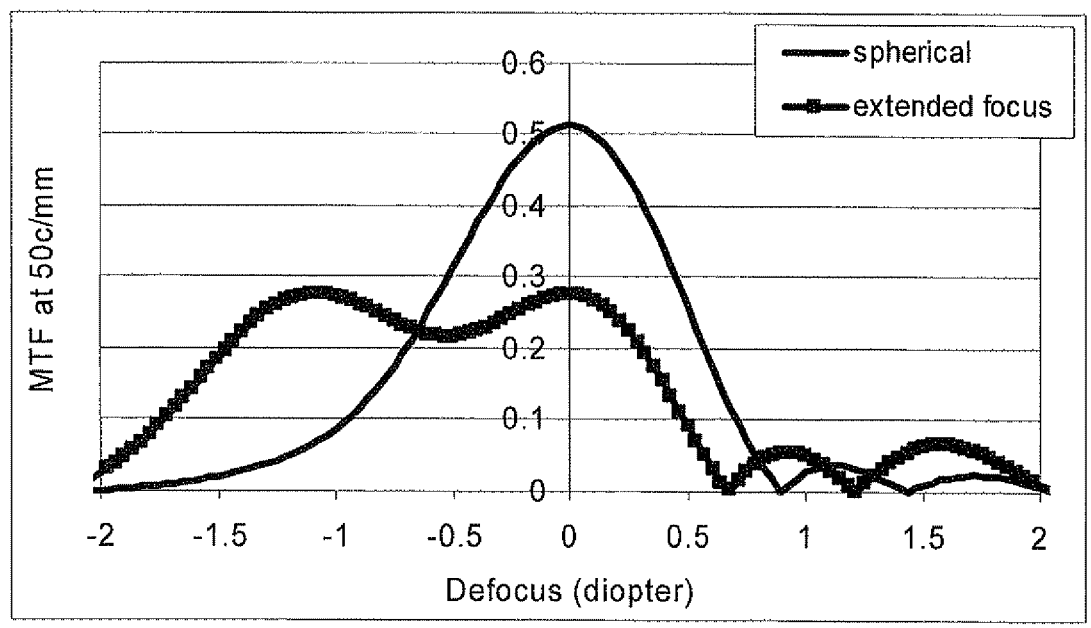
FIG. 23 is a through-focus plot of the calculated Modulation Transfer Function at 50 lp/mm for the intraocular lens of FIG. 21 used in the Liou-Brennan model eye of FIG. 22.

FIG. 23 shows the performance of the "extended focus" lens of FIG. 21, used in the system of FIG. 22, compared to the performance of a similar "refractive" lens that does not have the 1.2-Diopter-add-power diffractive element. FIG. 23 is a through-focus plot of the simulated Modulation Transfer Function at 50 line pairs per mm (or, equivalently, cycles per mm or c/mm) for the "spherical" and "extended focus" intraocular lenses described above.

The "extended focus" lens has a reduced peak MTF, but an increased width to the MTF curve, compared to the "refractive" lens. The depth of focus may be defined in a number of ways, and many definitions show this increased width. Two exemplary depth of focus definitions are considered below.

A first definition of depth of focus uses an absolute threshold value of 0.17, where the depth of focus is the power range over which the MTF at 50 c/mm exceeds 0.17. Using this definition, the "refractive" lens has a depth of focus of 1.36 Diopters, and the "extended focus" lens has a depth of focus of 1.90 Diopters, which is about 39% larger than the "refractive" lens.

A second definition of depth of focus uses an absolute threshold value of 0.20, where the depth of focus is the power range over which the MTF at 50 c/mm exceeds 0.20. Using this definition, the "refractive" lens has a depth of focus of 1.25 Diopters, and the "extended focus" lens has a depth of focus of 1.72 Diopters, which is about 37% larger than the "refractive" lens.

Similarly, other definitions for depth of focus may be used, many of which also show the substantial increase in depth of focus of the "extended focus" lens (which includes a diffractive element with 1.2 Diopter add power) over the "refractive" lens (a similarly-shaped lens that does not include the diffractive element).

The simulated results for Liou-Brennen model may correspond to the surface spacings and shapes of an idealized real eye, but they are difficult to verify experimentally because the lens would be surgically implanted inside the eye of a patient Accordingly, there is a second eye model, the so-called "Norrby modified ISO model eye" or "Norrby model", which also may be simulated, but additionally allows for the measurement of a real lens on a physical testbed.

A second set of simulated results is presented below, which also confirms the increase in depth of focus for the "extended focus" lens over the "refractive" lens. This second simulation uses the "Norrby modified ISO model eye".

Figure 24:
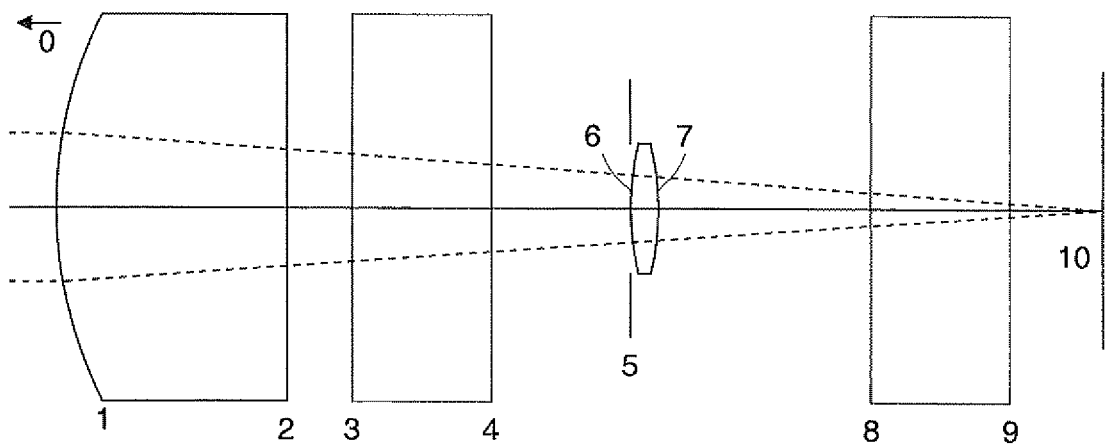
FIG. 24 is a surface-by-surface schematic drawing of a Norrby model eye with the intraocular lens of FIG. 21.

FIG. 24 is a surface-by-surface schematic drawing of the simulated eye systems for the Norrby model. The dotted lines in FIG. 24 represent rays from an infinitely distant object, passing through the zeroth order of the diffractive element and forming a "far" focus at the retina. There are ten surfaces in the simulated Norrby eye, with a number 0 surface located infinitely far away. Each surface is described below.

Surface 0 may be considered to be the object of the system. Surface 0 is infinitely far away, or any suitable approximation of infinity, such as 1e9 mm or 1e20 mm. The material after surface zero is air, with a refractive index of 1.

Surfaces 1 and 2 are the anterior and posterior surfaces of a plano-convex singlet that mimics the performance of a typical cornea. Surface 1 is the anterior surface of the plano-convex singlet, with a radius of curvature of +19.24 mm and a conic constant (also known as "asphericity" or Q-value) of +0.226. The refractive index between surface 1 and surface 2 is the refractive index of the singlet, with a value of about 1.493 at a wavelength of 546 nM. The separation between surface 1 and surface 2 is the thickness of the singlet, 10 mm. Surface 2 is essentially flat or planar. The singlet has a focal length in air of about 39 mm, or, equivalently, a power in air of about 25.6 Diopters.

The refractive index between surface 2 and surface 3 is 1. The separation between surface 2 and surface 3 is 3 mm.

Surfaces 3 and 4 are the anterior and posterior surfaces of a window. Both surfaces 3 and 4 are flat. The window is made of BK7 glass, which has a refractive index of about 1.517 at 546 nm. Alternatively, other glasses may be used, such as SF11, LaSFN9, BaK1, F2, fused silica, or any other suitable glass type. The separation between surfaces 3 and 4 is the window thickness, with a value of 6 mm.

The refractive index between surface 4 and surface 5 is roughly equal to that of the aqueous in an actual eye, with a value of about 1.336 at a wavelength of 546 nm. The separation between surface 4 and surface 5 is 6.25 mm.

Surface 5 is the iris of the eye, and is the aperture stop of the simulated optical system. It has a radius proportional to the pupil diameter, and has no power or curvature. The pupil diameter in the simulations is 3 mm.

The refractive index between surface 5 and surface 6 is about 1.336 at a wavelength of 546 nm. The separation between surface 5 and surface 6 is 0.

Surface 6 is the anterior surface of the intraocular lens, with a radius of curvature of +12.154 mm.

The refractive index between surface 6 and surface 7 is the refractive index of the intraocular lens. The lens is made of a silicone material, with a value of about 1.46 at a wavelength of 546 nm. The separation between surface 6 and surface 7 is the axial thickness (or "center thickness") of the lens, 1 mm.

Surface 7 is the posterior surface of the intraocular lens, with a radius of curvature of −12.154 mm. Note that the lens is bi-convex and symmetrical, with a conic constant of 0 and no aspheric terms. In other words, the shape of the anterior and posterior surfaces is spherical. Alternatively, the anterior and/or posterior surfaces of the lens may include a non-zero conic constant or one or more aspheric terms.

For the "refractive" lens used as a benchmark in this comparison, the optic includes surfaces 6 and 7 as described above. For the "extended focus" lens, surface 7 also includes a parabolic, blazed diffractive profile, imposed on the shape of the surface.

The blazed profile for the Norrby simulation is similar to that described in the Liou-Brennan simulation, only with the radius of the first ring in the diffractive profile being 1.0 mm, corresponding to an add power of 1.1 Diopters, and a depth of the profile being 3.3 microns.

The refractive index between surface 7 and surface 8 is about 1.336 at a wavelength of 546 nm. The separation between surface 7 and surface 8 is 9 mm.

Surfaces 8 and 9 are the anterior and posterior surfaces of a second window, similar in thickness (6 mm) and refractive index (1.517) to the window between surfaces 3 and 4.

The refractive index between surface 9 and surface 10 is 1.

The thickness between surface 9 and surface 10 may be set to a "solve" in a raytrace program, such as OSLO or ZEMAX, and is about 3.4 mm.

Surface 10 is the retina, and is the image plane for the simulated optical system.

The Norrby eye model was evaluated in monochromatic light at a wavelength of 546 nm.

Figure 25:
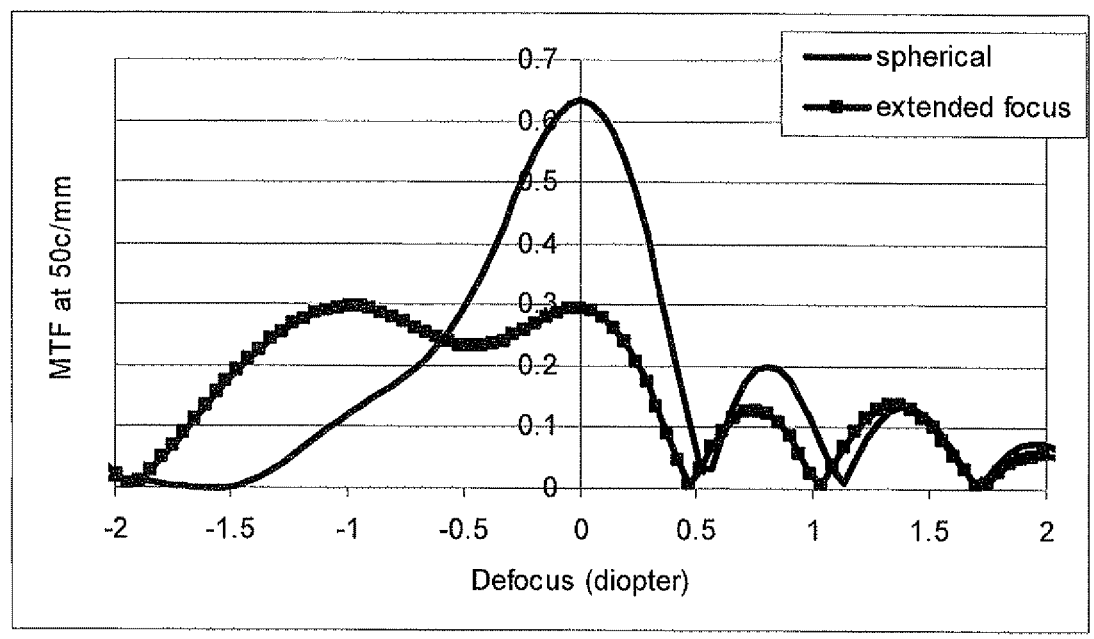
FIG. 25 is a through-focus plot of the calculated Modulation Transfer Function at 50 lp/mm for the intraocular lens of FIG. 21 used in the Norrby model eye of FIG. 24.

FIG. 25 shows the performance of the "extended focus" lens of FIG. 21, used in the system of FIG. 24, compared to the performance of a similar "refractive" lens that does not have the 1.1-Diopter-add-power diffractive element. FIG. 25 is a through-focus plot of the simulated Modulation Transfer Function at 50 c/mm for the "spherical" and "extended focus" intraocular lenses described above.

The performances of both lenses in the Norrby eye model (FIG. 25) are similar to those in the Liou-Brennen eye model (FIG. 23). The "extended focus" lens has a reduced peak MTF, but an increased width to the MTF curve, compared to the "refractive" lens. As with the Liou-Brennan simulation, the Norrby simulation considers two exemplary definitions for depth of focus.

A first definition of depth of focus uses an absolute threshold value of 0.17, where the depth of focus is the power range over which the MTF at 50 c/mm exceeds 0.17. Using this definition, the "refractive" lens has a depth of focus of 1.18 Diopters, and the "extended focus" lens has a depth of focus of 1.80 Diopters, which is about 52% larger than the "refractive" lens.

A second definition of depth of focus uses an absolute threshold value of 0.20, where the depth of focus is the power range over which the MTF at 50 c/mm exceeds 0.20. Using this definition, the "refractive" lens has a depth of focus of 1.04 Diopters, and the "extended focus" lens has a depth of focus of 1.66 Diopters, which is about 59% larger than the "refractive" lens.

The Norrby model is conducive to testing real lenses in a physical testbed, which is described in the following four paragraphs.

The lens under test is placed against the iris, so that the anterior surface of the lens becomes roughly coincident with the aperture stop of the test system. The lens under test is immersed in a fluid that mimics the fluids in the eye, and the lens and fluids are contained in a chamber bounded by the first and second windows. The light comes to focus outside the chamber, in air. In practice, the separation between the second window (surface 9) and the image plane or detector (surface 10) may be adjusted, depending on the properties of the lens under test.

It should be noted that the refractive index of the fluid in the eye model has an influence on the measured MTF of diffractive lenses. In order to simulate the in vivo situation, the difference in refractive index between the lens material and the eye's aqueous humor (at 35° Celsius and in equilibrium with water) should be the same as under the test conditions in the eye model.

In the Norrby simulation, an aqueous fluid was used with a refractive index of 1.336. For other lens designs, other refractive indices may be more appropriate. Specifically, using different materials may require different refractive indices of the aqueous fluid. For example, consider a material "A", which has no water uptake, a refractive index of 1.5 at 546 nm and 22° C. and a decrease of refractive index of 0.0003/° C. As a result, the refractive index of "A" in vivo would be 1.496 (at 35° C.) and the difference between the refractive indices of the eye and the lens would be 1.496−1.336=0.160. In order to have the same difference under the test conditions at 22° C., the aqueous fluid should have a refractive index of 1.5−0.16=1.340. A similar approach can be applied in case that water uptake of the lens material influences the refractive index of the lens.

As an alternative for changing the refractive index of the fluid in the eye model, the measurements can be performed at 35° C., with the lens in equilibrium with water and with the fluid having the standard refractive index of 1.336.

It is instructive to summarize the simulations performed with both the Liou-Brennan and Norrby eye models. It is found that the addition of a diffractive element with a fairly low add power can increase the depth of the focus of an intraocular lens, compared to a similarly shaped intraocular lens without the diffractive element. The add power of the diffractive element can be in the ranges of 0.5 to 2.5 Diopters, or 1.0 to 2.0 Diopters, or 1.5 to 2.0 Diopters, or 1.0 to 1.5 Diopters. In one embodiment, the depth of focus is defined in terms of a threshold MTF value at a particular spatial frequency. The threshold may be an absolute threshold, such as 0.10, 0.15, 0.17, 0.20, 0.25 or 0.30, or may be a relative threshold, such as a particular percentage of the peak value. The spatial frequency may be 25 line pairs per mm, 50 line pairs per mm, 100 line pairs per mm, or any suitable value.

The preceding embodiments are merely for illustrative purposes, and should not be construed as limiting in any way. The above model parameters may be adjusted to suit a particular set of design objectives or to reflect a particular set of measurements for a particular set of eyes or an individual eye. For example, the parameters for the eye model may be selected based on statistical averages for a particular population, such as disclosed in U.S. Pat. No. 6,705,729, which is herein incorporated by reference in its entirety. In addition, the design of the diffractive element may be adjusted to provide a predetermined visual response within the eye of a subject or patient. The add power between the diffractive orders of the intraocular lens is generally less than that of a substantially equivalent prior art multifocal, preferably less than about 3 Diopters, more preferably less than 2.5 Diopter, less than 2 Diopters, or less than or equal to about 1 Diopter. In some embodiments, the add power may be selected to between about 0.5 Diopters and about 1.5 Diopters. Alternatively, even smaller add powers may be utilized, for example, less than about 0.5 Diopters.

In addition, the diffractive element may be configured to use other diffractive orders besides the zeroth and +1 diffractive orders, for example, the +1 and +2 diffractive orders or the −1 and +1 diffractive orders. Alternatively, the diffractive element may be a combined grating or may comprise more than one physical grating surface, for example, as disclosed in U.S. Pat. No. 5,117,306, which is herein incorporated by reference in its entirety. In other embodiments, the diffractive element provides a lower add power over only a portion of the lens aperture, for example, similar to the configurations disclosed in U.S. Pat. No. 7,188,949, which is also herein incorporated by reference in its entirety.

For many of the examples provided in this document, we defined the depth of focus as the region in a through-focus plot over which the Modulation Transfer Function (MTF) at a spatial frequency of 50 line pairs per mm exceeded a cutoff value of 0.17. In some embodiments, the definition of depth of focus may be based on a different cutoff (e.g., a cutoff value of about 0.15, about 0.20, or about 0.25) or a different spatial frequency (e.g., a spatial frequency of about 25 line pairs per mm or about 100 line pairs per mm). The depth of focus may be alternatively defined in terms of axial distance, or, equivalently, in terms of power, as shown in FIG. 4. There are many possible alternative definitions of depth of focus that many be used, as well as many other figures of merit that may be used for the definitions.

The figures of merit, or metrics, may be either purely optical in nature, or may incorporate some perception effects from the human eye.

For instance, any or all of the following optical metrics may be used: MTF at a particular spatial frequency, MTF volume (integrated over a particular range of spatial frequencies, either in one dimension or in two dimensions), Strehl ratio, encircled energy, RMS spot size, peak-to-valley spot size, RMS wavefront error, peal-to-valley wavefront error, and edge transition width.

Alternatively, any of the following psychophysical metrics may be used: contrast sensitivity, visual acuity, and perceived blur. In addition, many more metrics may be found in the literature, such as those detailed in Marsack, J. D., Thibos, L. N. and Applegate, R. A., 2004, "Metrics of optical quality derived from wave aberrations predict visual performance," J Vis, 4 (4), 322-8; and Villegas, E. A., Gonzalez, C., Bourdoncle, B., Bonnin, T. and Artal, P., 2002, "Correlation between optical and psychophysical parameters as a function of defocus," Optom Vis Sci, 79 (1), 60-7. All of these references are herein incorporated by reference in their entirety.

Any or all of these metrics may be defined at a single wavelength such as 550 nm or any other suitable wavelength, or over a larger spectral region, such as the visible spectrum from 400 nm to 700 nm. The metrics may be weighted over a particular spectral region, such as the weighting associated with the spectral response of the human eye.

Given the many possible figures of merit, there are several ways to evaluate them to define a depth of focus.

One way is to define an absolute threshold, where the crossings of the figure of merit with the threshold define the depth of focus. For instance, the depth of focus may be defined as the region over which the MTF at 50 lp/mm exceeds a threshold of 0.17. Alternatively, any suitable MTF absolute threshold may be used, such as 0.1, 0.15, 0.2, 0.25, 0.3 and so forth. Alternatively, the depth of focus may be defined as the region over which the RMS spot size is less than a particular threshold value.

Another way is to define the depth of focus is based on a relative threshold, where the threshold is defined based on a peak value of the figure of merit. For instance, the depth of focus may be defined as the full width at half max (FWHM) of the MTF at a particular spatial frequency. Other relative thresholds may be 95%, 90%, 80%, 70%, 60%, 50%, 1/e, $1/e^2$, or any suitable fraction of the peak value of the metric.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intraocular lens, comprising:
an optic including a first surface having a first shape and an opposing second surface having a second shape, the first and second shapes providing a refractive power;
a diffractive pattern imposed on at least one of the first shape and the second shape with a concentric central zone having a center and a plurality of concentric zones surrounding the central zone wherein the central zone and the plurality of concentric zones are each comprised of an edge with a step discontinuity at the edge having a step height between about 1 micron and 3.3 microns, wherein the central zone is configured such that the edge of the central zone is 360° out of phase with the center of the central zone; and wherein
the first and second surfaces provide a base power and an add power that is between 0.5 Diopter and 1.5 Diopter so that the intraocular lens has a depth of focus that exceeds that of any single focus of a similar spherical lens having an optical power equal to the base power of the intraocular lens.

2. The intraocular lens of claim 1, wherein the central zone radius is equal to or about 1.05 mm.

3. The intraocular lens of claim 1, wherein the add power is equal to about one Diopter.

4. The intraocular lens of claim 1, wherein the diffractive pattern has a first diffracted order providing a first diffractive power, the base power being determined at least in part by the refractive power, the add power being determined at least in part by the first diffractive power.

5. The intraocular lens of claim 1, wherein the diffractive pattern has a nth diffracted order providing a first diffractive power and a (n+1)th diffracted order providing a second diffractive power, the base power being determined at least in part by the refractive power and the first diffractive power, the add power being determined at least in part by the difference between the second diffractive power and the first diffractive power.

6. The intraocular lens of claim 1, wherein at least one of the first and second shapes has an aspheric component.

7. The intraocular lens of claim 1, wherein the diffractive pattern has a plus first diffracted order providing a first diffractive power and a minus first diffracted order providing a second diffractive power, the base power being determined at least in part by the refractive power and the first diffractive power, the add power being determined at least in part by the difference between the second diffractive power and the first diffractive power.

8. The intraocular lens of claim 1, wherein the base power and the add power are formed from adjacent diffracted orders, respectively, from the diffractive pattern.

9. The intraocular lens of claim 1, wherein the base power and the add power result in a first focus and a second focus that have equal intensities.

10. The intraocular lens of claim 1, further comprising first and second foci formed from different diffracted orders.

11. An intraocular lens, comprising:
an optic including a first surface having a first shape and an opposing second surface having a second shape, the first and second shapes providing a refractive power;
a diffractive pattern imposed on at least one of the first shape and the second shape with a concentric central zone having a center and a plurality of concentric zones surrounding the central zone wherein the central zone and the plurality of concentric zones are each comprised of an edge with a step discontinuity at the having a step height between about 1 micron and 3.0 microns, wherein the central zone is configured such that the edge of the central zone is 360° out of phase with the center of the central zone; and wherein the first and second surfaces provide a base power and an add power that is between 0.5 Diopter and 1.5 Diopter such that when the intraocular lens is optically described by a model lens, and the model lens is included in an intraocular lens plane of an eye model including a model cornea, a design wavelength of 550 nm, and a pupil radius of 1.5 mm, the eye model has an extended depth of focus characterized by a modulation transfer function that exceeds 0.17, at a spatial frequency of 50 line pairs per millimeter, over a range of at least about 1.7 Diopters.

12. The intraocular lens of claim 11, wherein the eye model is a Liou-Brennan eye model or a Norrby Modified ISO eye model.

13. The intraocular lens of claim 11, wherein the modulation transfer function of the eye model exceeds about 0.20, at a spatial frequency of 50 line pairs per millimeter, over a range of at least about 1.9 Diopters.

14. An intraocular lens, comprising:
an optic comprising a first surface having a first shape and an opposing second surface having a second shape, the first and second shapes providing a refractive power;
a diffractive pattern imposed on at least one of the first shape and the second shape with a concentric central zone having a center and a plurality of concentric zones surrounding the central zone wherein the central zone and the plurality of concentric zones are each comprised of an edge with a step discontinuity at the edge having a step height between about 1 micron and 3.0 microns, wherein the central zone is configured such that the edge of the central zone is 360° out of phase with the center of the central zone; and wherein the first and second surfaces provide a base power and an add power that is between 0.5 Diopter and 1.5 Diopter such that when the optic is placed in an intraocular lens plane of a physical eye model including a model cornea, a design wavelength of 550 nm, and a pupil radius of 1.5 mm, the eye model has an extended depth of focus characterized by a modulation transfer function that exceeds 0.17, at a spatial frequency of 50 line pairs per millimeter, over a range of at least about 1.7 Diopters.

15. The intraocular lens of claim 14, wherein the eye model is a Norrby Modified ISO eye model.

16. An intraocular lens, comprising:
an optic including a first surface having a first shape and an opposing second surface having a second shape, the first and second shapes providing a refractive power;
a diffractive pattern imposed on the first shape or the second shape with a concentric central zone having a center and a plurality of concentric zones surrounding the central zone wherein the central zone and the plurality of concentric zones are each comprised of an edge with a step discontinuity at the edge having a step height between about 1 micron and 3.0 microns, wherein the central zone is configured such that the edge of the central zone is 360° out of phase with the center of the central zone such that the intraocular lens has an extended depth of focus characterized by a depth of focus that is at least about 30% greater than that of a reference lens without a diffractive pattern, the reference lens having a refractive power that is equal to the base power of the intraocular lens.

17. The intraocular lens of claim 16, wherein the light source is a polychromatic light source.

18. The intraocular lens of claim 17, wherein the polychromatic light source is described by a Liou-Brennan eye model.

19. The intraocular lens of claim 16, wherein the light source is at a predetermined wavelength and the intraocular lens has a depth of focus, when illuminated at the predetermined wavelength, that is at least about 50% greater than that of the intraocular reference lens.

20. The intraocular lens of claim 19, wherein the predetermined wavelength is about 546 nm.

21. The intraocular lens of claim 16, wherein, at a spatial frequency of about 50 line pairs per millimeter, the modulation transfer function of the lens exceeds 0.17 over a depth of focus that is greater than the depth of focus for the reference intraocular lens by at least about 0.5 Diopters.

22. The intraocular lens of claim 16, wherein the intraocular lens is optically described by a model lens, such that when the model lens is included in an intraocular lens plane of an eye model including a model cornea, the modulation transfer function of the eye model exceeds about 0.17, at a spatial frequency of about 50 line pairs per millimeter, over a focal range of at least about 1.7 Diopters.

* * * * *